US012697364B2

(12) United States Patent
Rodriguez Vilaboa

(10) Patent No.: US 12,697,364 B2
(45) Date of Patent: Aug. 4, 2026

(54) COMPOSITION FOR THE PREVENTION AND TREATMENT OF DYSBIOSIS

(71) Applicant: MUCOSA INNOVATIONS, S.L., Madrid (ES)

(72) Inventor: Deborah Rodriguez Vilaboa, Madrid (ES)

(73) Assignee: MUCOSA INNOVATIONS, S.L., Madrid (ES)

( * ) Notice: Subject to any disclaimer, the term of this patent is extended or adjusted under 35 U.S.C. 154(b) by 650 days.

(21) Appl. No.: 17/904,747

(22) PCT Filed: Feb. 26, 2021

(86) PCT No.: PCT/EP2021/054896
§ 371 (c)(1),
(2) Date: Aug. 22, 2022

(87) PCT Pub. No.: WO2021/170834
PCT Pub. Date: Sep. 2, 2021

(65) Prior Publication Data
US 2023/0041103 A1 Feb. 9, 2023

(30) Foreign Application Priority Data

Feb. 28, 2020 (EP) .................................... 20382147

(51) Int. Cl.
| | |
|---|---|
| *A61K 36/63* | (2006.01) |
| *A61K 31/047* | (2006.01) |
| *A61K 31/205* | (2006.01) |
| *A61P 1/00* | (2006.01) |

(52) U.S. Cl.
CPC ............ *A61K 36/63* (2013.01); *A61K 31/047* (2013.01); *A61K 31/205* (2013.01); *A61P 1/00* (2018.01)

(58) Field of Classification Search
None
See application file for complete search history.

(56) References Cited

FOREIGN PATENT DOCUMENTS

| | | | |
|---|---|---|---|
| CN | 105748368 A | | 7/2016 |
| CN | 106176543 A | | 12/2016 |
| CN | 106389178 A | | 2/2017 |
| CN | 109953933 A | | 7/2019 |
| EP | 2119477 A1 | | 11/2009 |
| EP | 3400935 A1 | * | 11/2018 |
| ES | 2051238 A1 | | 6/1994 |
| ES | 2663574 | | 4/2018 |
| RU | 2115327 C1 | * | 7/1998 |
| UA | 108535 U | * | 7/2016 |
| WO | WO 2008/142178 | | 11/2008 |
| WO | WO 2019/025366 | | 2/2019 |
| WO | WO 2020/025657 | | 2/2020 |

OTHER PUBLICATIONS

International Search Report and Written Opinion for PCT/EP/2021/054896. Mailed May 14, 2021. 9 pages.
Atarashi et al., Ectopic colonization of oral bacteria in the intestine drives TH1 cell induction and inflammation. Science. Oct. 20, 2017;358(6361):359-365.
Dawes. What is the critical pH and why does a tooth dissolve in acid? J Can Dent Assoc. Dec. 2003;69(11):722-4.
Hezel et al., The oral microbiome and nitric oxide homoeostasis. Oral Dis. Jan. 2015;21(1):7-16.
Lee et al., Potential Role of the Microbiome in Acne: A Comprehensive Review. J Clin Med. Jul. 7, 2019;8(7):987. 1-25.
Lira-Junior et al., Oral-gut connection: one step closer to an integrated view of the gastrointestinal tract. Mucosal Immunol. Mar. 2018;11(2):316-318.
Lussi et al., The future of fluorides and other protective agents in erosion prevention. Caries Res. 2015:49 Suppl 1:18-29.
Martin et al., Products based on olive oil, betaine, and xylitol in the post-radiotherapy xerostomia. Rep Pract Oncol Radiother. Jan.-Feb. 2017;22(1):71-76.
Paju et al., Oral biofilms, periodontitis, and pulmonary infections. Oral Dis. Nov. 2007;13(6):508-12.
Segata et al., Composition of the adult digestive tract bacterial microbiome based on seven mouth surfaces, tonsils, throat and stool samples. Genome Biol. Jun. 14, 2012;13(6):R42. 1-18.
Sudhakara et al., Oral Dysbiotic Communities and Their Implications in Systemic Diseases. Dent J (Basel). Apr. 16, 2018;6(2):10.
Szántó et al., Targeting the gut-skin axis-Probiotics as new tools for skin disorder management? Exp Dermatol. Nov. 2019;28(11):1210-1218.
Van Dyke. Pro-resolving mediators in the regulation of periodontal disease. Mol Aspects Med. Dec. 2017:58:21-36.
Vaughn et al., Skin-gut axis: The relationship between intestinal bacteria and skin health. World Journal of Dermatology, 2017; 6(4):52-58.
Wallen-Russell. The role of every-day cosmetics in altering the skin microbiome: A study using biodiversity. Cosmetics, 2019, 6(2). 1-22.
Yang et al., A common antimicrobial additive increases colonic inflammation and colitis-associated colon tumorigenesis in mice. Sci Transl Med. May 30, 2018;10(443):eaan4116.
López-López, J. et al. Rapid Reduction of Pro-Inflammatory Cytokines with an Oral Topical Composition Comprising Olive Oil, Trimethylglycine and Xylitol: A Randomized Double-Blind Controlled Trial. Int J Mol Sci. May 21, 2025;26(10):4920.

* cited by examiner

*Primary Examiner* — Michael V Meller
(74) *Attorney, Agent, or Firm* — Casimir Jones, S.C.; Rikki A. Hullinger

(57) ABSTRACT

The present invention refers to a composition for use in the prevention and/or treatment of dysbiosis. It also refers to the use of said composition for preparing a medicament for the prevention and/or treatment of dysbiosis. Furthermore, it refers to a method of preventing and/or treating of dysbiosis in which said composition is administered to a subject in need thereof.

16 Claims, 3 Drawing Sheets

COMPOSITION FOR THE PREVENTION AND TREATMENT OF DYSBIOSIS

FIELD OF THE INVENTION

Figures 1A, 1B:
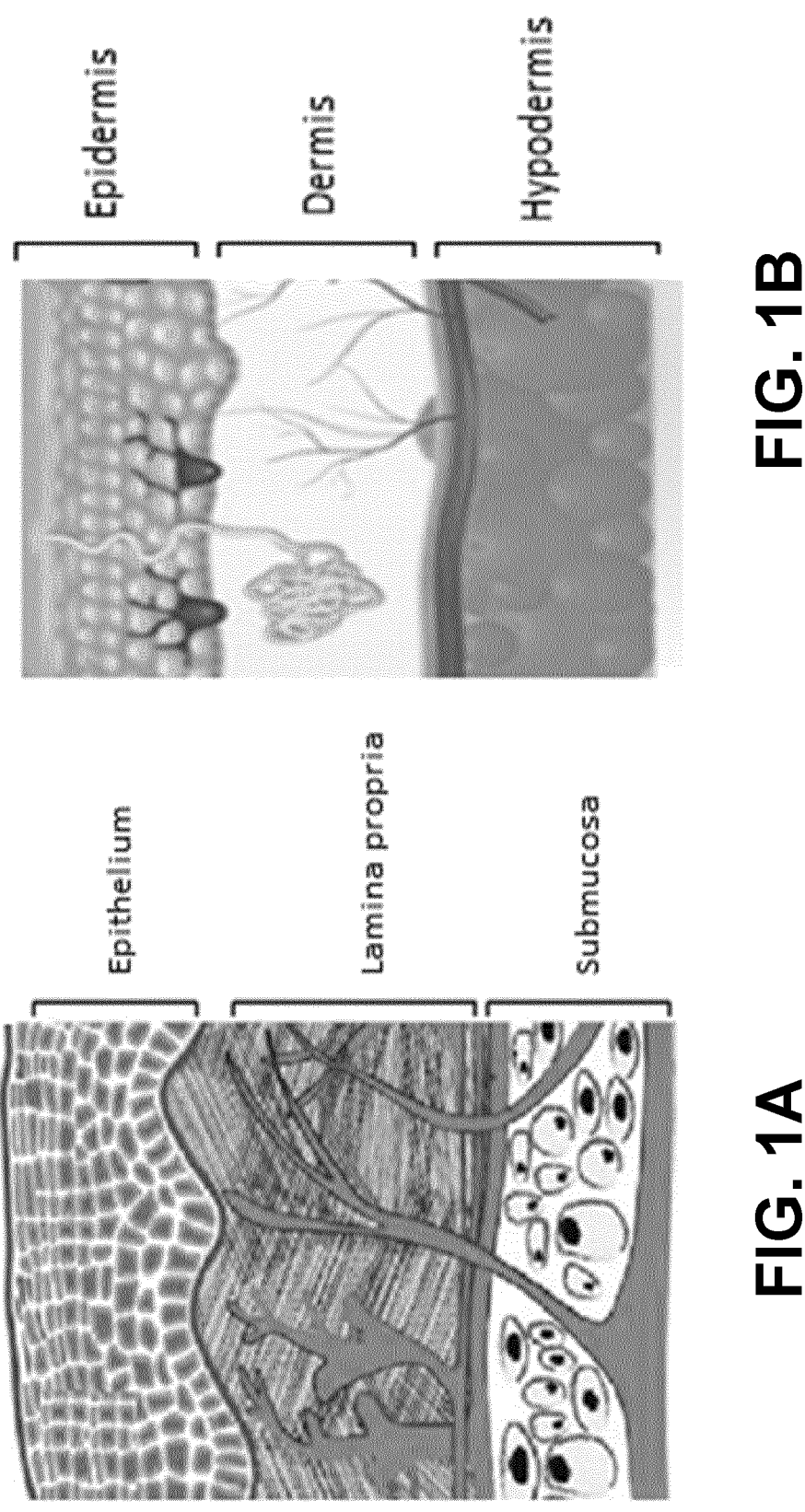

The present invention refers to the field of microbiome and its relation to health and disease. In particular, it refers to a composition for use in the prevention and treatment of dysbiosis.

BACKGROUND OF THE INVENTION

Microbiome and microbiota are sometimes used as similar terms. Microbiota means the set of microorganisms composed by bacteria, fungi, archaea, viruses and parasites that live in or on our body while microbiome is a wider term that refers to the whole habitat including not only microorganisms but also their genes and metabolites and their ecosystem. This invisible to the eye architectural 3D structure relies in an extra cellular matrix that serves as a physicochemical scaffold for the biofilms and, in view of the current inventors, is key to the onset of dysbiosis and the recovery of health (eubiosis). Not only this scaffold has chemical properties but also physically it contributes to the shape of this universe providing protection from environmental offences (changes in humidity, pH shifts, temperature oscillation, antiseptics, antibacterials, stress between others). Ideally, it should also house the necessary for cell life, that is water, nutrients and restrict penetration of detrimental agents.

Biofilms are understood as the specific microbiota and its ecosystem that lives in the different parts of the body attached to a particular surface organized three dimensionally. Examples of biofilms are oral, dental, skin and vagina biofilm.

The microbiota install themselves progressively in or on the body upon birth depending on the channel of birth (vaginal or cesarean), mother's microbiome, type of nutrition, geography, habits, psychology and lifestyle. It confers an individual personality to the host, stablishing a bidirectional conversation between the host and the microbiota and vice versa. Life style, stress, education, character, age, geography, climate, are known to change the microbiota and its ecosystem and, at the same time, the microbiota may change the ecosystem and then ultimately the individual. Medications, tobacco and alcohol, stress, wounds, mouth breathing, sleep apnea, eating disorders, and other systemic diseases, such as cancer and diabetes between others, impact negatively on the microbiome of the mucosa of the body in different sites such as mouth, lung, gut, vagina and skin giving place to an emerging portfolio of newly recognised and emerging dysbiosis of various severities.

Mucosa is a membrane lining of the body cavities and canals that lead to the outside, chiefly the respiratory, digestive and urogenital tracts. These include, amongst others, the mouth, nose, eyelids, trachea, lungs, stomach, intestines, ureters, urethra, vagina and the connections between the different locations. The mucosa of the body lines all ducts and tracts and shares common histological features and secretions of mucous that works as a barrier and is adapted to the different sites (papillae, microvilli, etc.). Skin exhibits also common histological features throughout the body and also has a barrier function with some adaptive particularities depending on the location (hair, sweat glands, etc.). Mucosa and skin are the most extensive microbiome habitat and the most susceptible to an imbalance or dysbiosis of the microbiome that connects the different sites.

The relation between dysbiosis and general health has been described by several studies giving birth to different schools of thinking advocating for connections between the different microbiomes originating what is today known as oral-gut axis, oral-liver axis, oral-lung axis, oral-gut-liver axis, oral-brain axis, oral-cardiovascular axis, gut-lung axis, gut-skin axis, oral-joint axis, oral-breast axis (Lira-Junior & Boström, 2018) and the herein newly described oral-skin axis (see below).

Regarding the oral-lung axis, periodontitis dysbiosis as a source of inflammatory mediators has been related to exacerbation of lung disease (Paju & Scannapieco, 2007). Increasing evidence on the role of the lung microbiome and its impact on the progression and severity of lung diseases has been studied in different groups such as pneumonia, cold, influenza, cystic fibrosis, pulmonary fibrosis, chronic obstructive pulmonary disease (COPD).

Evidence of a Gut-Skin Axis through inflammatory diseases of skin associated to gut microbiome imbalance has been translated so far to the recognition of the potential benefit of probiotics to improve skin conditions through gut microbiome (Atarashi, Wataru, & Chengwei, 2017). Transplant measures have emerged lately in an attempt to replicate this sub universe from healthy individuals (donors) to sick subjects (receptors). Similarly, some clinicians have advocated for skin microbiota transplantation of healthy subjects to ameliorate the symptoms and clinical course of Atopic Dermatitis instead of antibiotics against the pathogen *S. aureus*. Unfortunately, microbiome transplant therapies need further development, appear an expensive approach and so far, have little practical application left to hospital environment and seem far for becoming everyday practice.

So far, attempts to correct dysbiotic deleterious microbiome by means of supplantation or transplantation (probiotics science) or eradication (antibiotics therapy) have demonstrated uncertain safety and effectivity issues. Therefore, there is still a need for improved therapies for prevention and treatment of dysbiosis.

OBJECT OF THE INVENTION

A first aspect of the present invention refers to a composition comprising an olive product, betaine and xylitol for use in the prevention and/or treatment of dysbiosis, wherein the olive product is olive oil and/or olive fruit extract.

A second aspect of the present invention refers to the use of a composition comprising an olive product, betaine and xylitol for the preparation of a medicament for the prevention and/or treatment of dysbiosis, wherein the olive product is olive oil and/or olive fruit extract.

A third aspect of the present invention refers to a method of treating dysbiosis in a subject in need thereof, comprising administering a therapeutically effective amount of a composition comprising an olive product, betaine and xylitol, wherein the olive product is olive oil and/or olive fruit extract.

A fourth aspect of the present invention refers to a method of preventing dysbiosis in a subject which comprises administering to the subject a prophylactically effective amount of a composition comprising an olive product, betaine and xylitol, wherein the olive product is olive oil and/or olive fruit extract.

A fifth aspect of the invention refers to the use of a composition comprising an olive product, betaine and xylitol for the hygiene of the oral cavity, nasal cavity, vagina and/or the skin, and to the use for maintaining natural hydration of the mucosa and/or skin of the human body, wherein the olive product is olive oil and/or olive fruit extract.

Other objects, features, advantages and aspects of the present application will become apparent to those skilled in the art from the following description and appended claims.

BRIEF DISCUSSION OF THE FIGURES

FIG. 1. Schematic drawing of the skin and mucosa (oral mucosa) structure highlighting the similarities and parallelism between skin and mucosa.

Figure 2:
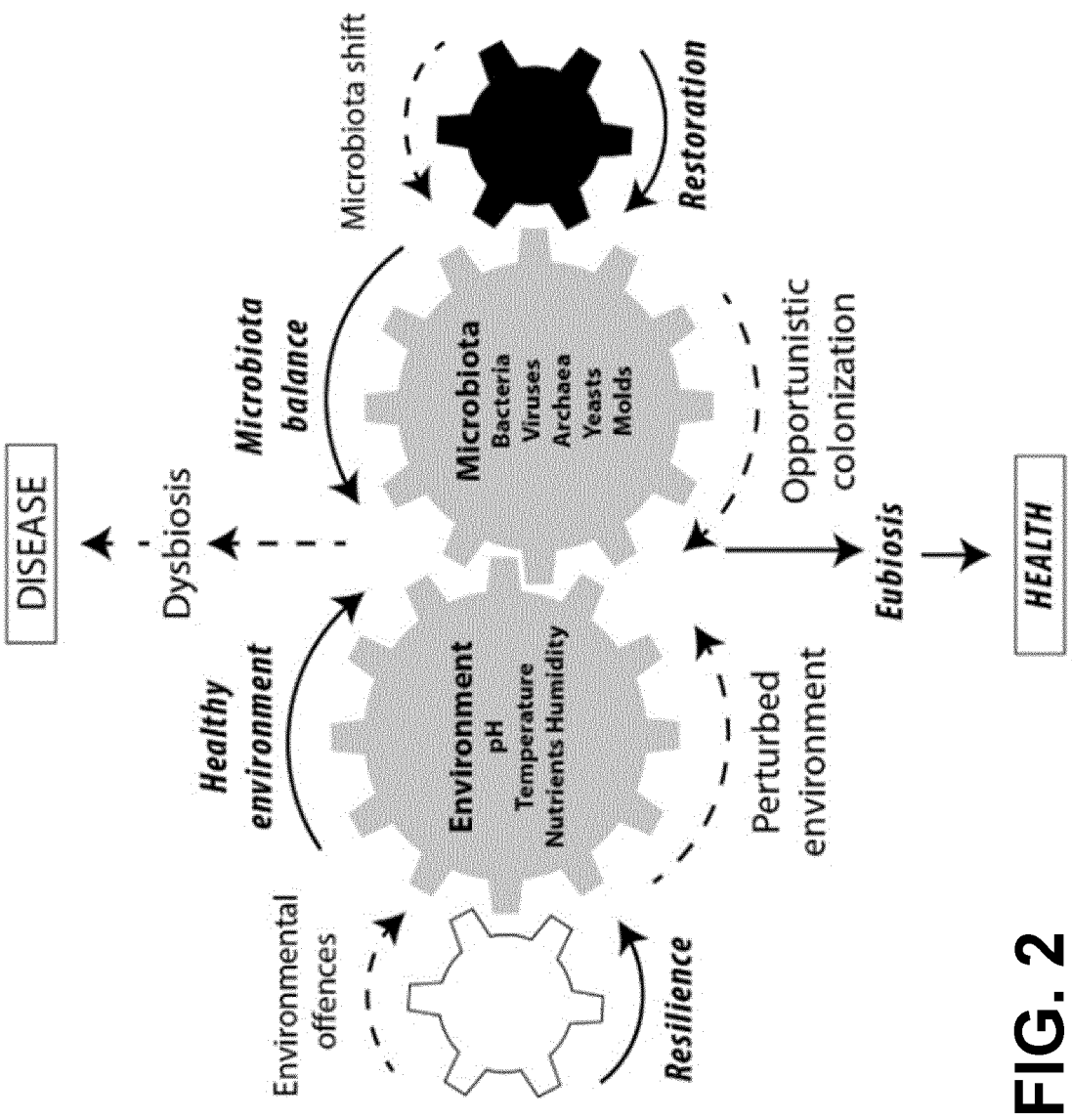

FIG. 2. Microbiome Dynamics Model of Eubiosis and Dysbiosis. The ecosystem is part of the microbiome self-reparatory cycle to promote symbiosis (health) and prevent dysbiosis (disease) but also actor in the Microbiome Vicious Circle to perpetuate dysbiosis.

Figure 3:
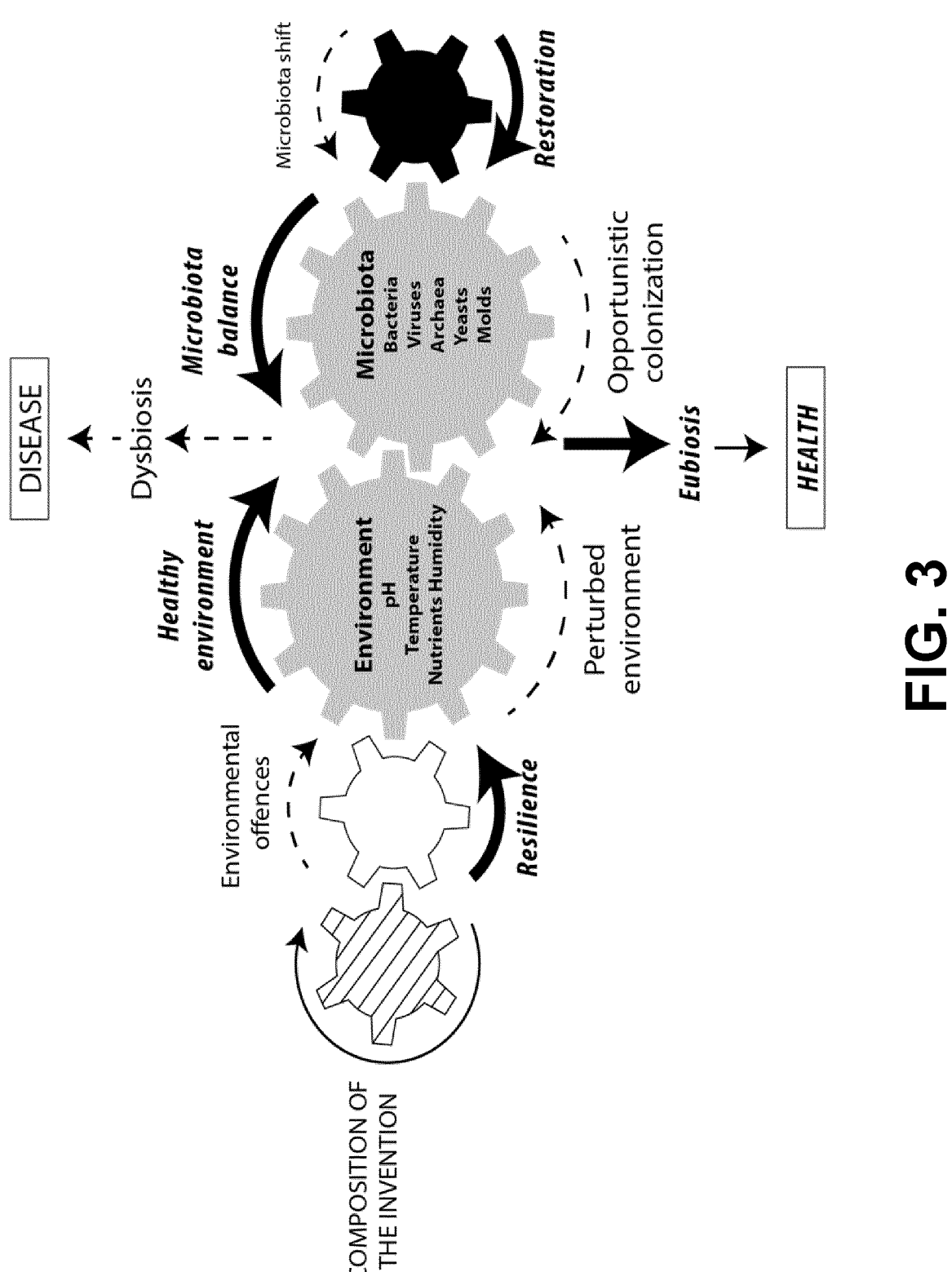

FIG. 3. Microbiome Dynamics with the composition of the invention. The composition of the invention enhances the resilience of the ecosystem promoting a healthy environment and a microbiota balance and eubiosis.

DETAILED DESCRIPTION OF THE INVENTION

As used herein, the singular forms "a," "an" and "the" include their corresponding plural forms unless the context clearly indicates otherwise. Unless defined otherwise, all the technical and scientific terms used herein have the same meaning as commonly understood by a person skilled in the art to which this invention belongs. To facilitate understanding and clarify the meaning of specific terms in the context of the present invention, the following definitions and particular and preferred embodiments thereof, applicable to all the embodiments of the different aspects of the present invention, are provided:

As used herein, "microbiome" refers to microbes that live in and on the human body and their genetic content, both sustainably and transiently, including eukaryotes, archaea, bacteria, and viruses (including bacterial viruses (i.e., phage)). "Genetic content" includes genomic DNA, RNA such as ribosomal RNA, the epigenome, plasmids, and all other types of genetic information. A healthy microbiome provides the host with multiple benefits, including colonization resistance to a broad spectrum of pathogens, essential nutrient biosynthesis and absorption, and immune stimulation that maintains a healthy epithelium and an appropriately controlled systemic immunity. The microbiome may be characterized in healthy individuals and those inflicted with disease. In healthy individuals, the microbiome is defined as normal.

Dysbiosis as opposite to eubiosis happens as a result of loss of balance within the microbiome either due to a shift in the microbiota or a change in the ecosystem of the microbiome.

"Dysbiosis" refers to a state of the microbiome of any area of the body, including mucosal and skin surfaces, in which the normal diversity or function of the ecological network is disrupted. Thus, in a particular embodiment, the dysbiosis is mucosa dysbiosis, skin dysbiosis or a combination thereof. Any disruption from the preferred (e.g., ideal, normal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis can be at the same time, cause or consequence of disease and may facilitate and/or aggravate the course of the disease. Dysbiosis may be due to a decrease in diversity, the overgrowth of one or more pathogens or pathobionts, symbiotic organisms able to cause disease only when certain genetic or environmental conditions are present in a patient, or the shift to an ecological network that no longer provides a beneficial function to the host and therefore no longer promotes health. Dysbiosis may be induced by illness (diabetes, cancer, infections, obesity, depression), treatment (e.g., overuse) with an agent (e.g., antibiotic, e.g., antibiotic reducing commensal flora), or other environmental factors (pH changes, inflammation, diet, medications).

In settings of "dysbiosis" or disrupted symbiosis, microbiome functions can be lost or deranged, resulting in increased susceptibility to pathogens, altered metabolic profiles, or induction of proinflammatory signals that can result in local or systemic inflammation or autoimmunity.

In a particular embodiment according to any one of the aspects of the invention, the dysbiosis is selected from mucosa dysbiosis, skin dysbiosis or a combination thereof.

In another particular embodiment according to any one of the aspects of the invention, the dysbiosis is selected from oral dysbiosis, lung dysbiosis, skin dysbiosis, and/or vagina dysbiosis.

"Oral dysbiosis" refers to a dysbiosis that affects part or all of the oral mucosa and/or teeth of a subject.

"Skin dysbiosis" refers to a dysbiosis that affects part or all the skin of a subject.

"Vagina dysbiosis" refers to vaginosis.

"Lung dysbiosis" refers to a dysbiosis that affects all or part of the mucosa in the lung and/or its vicinity (e.g. trachea).

The term "prevent" or "prevention" means preventing, delaying and/or reducing the severity of a disease and/or the signs and/or symptoms associated with a disease.

"Prophylactically effective amount" refers to an amount that when delivered, prevents, delays and/or reduces the severity of a disease and/or the signs and/or symptoms associated with a disease.

"Treatment" refers to the reduction or elimination of a disease and/or the signs and/or symptoms associated with a disease.

"Therapeutically effective amount" refers to an amount that is effective to reduce or eliminate a disease and/or the signs and/or symptoms associated with a disease.

Particularly, in the present invention, the disease is a dysbiosis or a pathology facilitated or exacerbated by dysbiosis.

Human Oral Microbiome Database (HOMD) has described the oral taxa and the phyla, strain, reaching to almost six hundred and twenty taxa out of which 65% have been cultured so far while in other sites of the body a scarce 1% have been cultivated. Firmicutes, Bacteroidetes, Proteobacteria, Actinobacteria, Spirochetes and Fusobacteria account for 95%. In skin the four dominant phyla are Actinobacteria, Proteobacteria, Firmicutes and Bacteroidetes. Both skin and oral cavity exhibit diverse topographic populations related to the different micro-environments. In the mouth the palate and lingual aspect of teeth call for different phyla to subgingival or buccal or tongue in a parallelism with the sebaceous environments of the upper parts of the body versus the phyla with higher diversity in the skin of the plies and the lower part of the body. Both skin and oral cavity have a high topographical diversity, dictated by the environment as said before with high temporal variability within the individual but, rather stable throughout life per an individual. The abundance focused by many researchers during the last years is today regarded only as relative marker of disease as all individuals will show *Staphylococcus, Propionibacterium* and *Corynebacterium* talking about skin, and *Streptococcus mutans* and *Porphyromonas gingivalis* when it comes to the mouth. Current research supports that pressing a habitual phyla Firmicutes of either skin (*Streptococcus epidermidis*) or mouth (*Streptococcus mutans*) makes it feasible for another Firmicutes of the phyla Staphylococci to penetrate skin making advantage of an inflammatory condition. In the mouth the shift imposed via anticaries agents that decrease the *Streptococcus mutans* population will lead to a decrease in acidic metabolites from these bacteria and enhance an increase in pH that will be used by asaccharolytic bacteria that prefer higher pH and lower oxygen gradient, that means anaerobic subgingival Gram-negative bacteria leading to periodontitis. Periodontitis is commonly associated to Staphylococci penetration in skin in patients with Oral Lichen Planus (OLP), a common chronic autoimmune mucocutaneous disease reported to be after oral ulceration the second most common oral mucosal disease. Twenty to thirty-five percent of OLP patients have lesions also in skin, scalp and/or vagina.

The most common microbiota of the oral cavity are *Streptococcus, Lactobacillus* and *Prevotella*. Respiratory bacterial analysis of patients with pneumonia with aspiration risks, showed that oral streptococci were the most common bacterial phyla detected both in the bronchi and lung.

In balanced non-inflammatory healthy conditions, both skin and mucosa exhibit barrier-like properties in the sense that the microbiome and the human cells are in different compartments across the whole extension of either tissue. An atomic separation between the microbiota and the host epithelial cells is needed for a symbiotic dual host-microbial interaction. When the skin or the mucosa is disrupted, like what is seen in wounds or inflammatory conditions, mechanisms lead to an altered relation between the host and the microbiome leading not only to a world of inflammatory dysbiotic diseases but also eventually to carcinogenesis. Research in the oral cavity is consistent today with the finding that oral dysbiosis and a dysbiotic biofilm is behind common highly prevalent diseases like caries and periodontitis. In view of the current investigators, teeth have their own microbiome that protects them from challenges as long as per symbiosis. At the same time teeth themselves, when healthy, are barrier to the maxillary bones from the moment they penetrate oral mucosa during eruption. When eventually a tooth is lost, mucosa takes its place and closes the gap as the barrier function is mandatory for human survival. As said before, for skin and mucosa, both the tooth and its microbiome are in different compartments physicochemically attached to one another and integrity of both compartments is mandatory for health and barrier function. When the microbiome is damaged, e.g. because of the separation and the integrity of both compartments is loss, disrupted or disappeared, a new dysbiotic relation between the host and the microbiome leads to a non-symbiotic inflammatory condition (periodontitis dysbiosis) or/and increased tooth permeability (hypersensitivity, demineralization, and loss of tooth structure). When this microbiome is lost, disrupted or damaged the barrier of the tooth is lost. Hypersensitivity, demineralization, caries and tooth wear either of physical, chemical or mix origin (bruxism, erosion, abfraction, attrition) happen. The disrupted microbiome barrier stops acting as a lipophilic shield and teeth start to dissolve in the acidic or extremely acidic media. Every mouth is different. The mineral content of teeth and the thickness of the enamel also varies between individuals. Other variables like salivary flow and mineral saturation of saliva explain altogether why some teeth will resist better than others calling this the critical pH (Dawes, 2003). In vitro conditions have ignored the living microbes and their ecosystem that may well be the major reservoir of minerals, water, peptides and proprietary metabolism that stop and prevent the human teeth from dissolving. This theory is supported by the fact that if there is no dental plaque, even stimulating saliva, will not be able to promote mineral deposition. In view of the current inventors a dysbiotic microbiome makes unfruitful the efforts to remineralize teeth by stimulating saliva or via supplementing minerals or remineralizing agents as some authors are starting to investigate (Lussi & Carvalho, The future of fluorides, 2015). When teeth are physically grinded and worn down, the habitat is changed as the initially hidden dentin emerges providing an altered support for the microbiome.

The more tooth wear and tooth structure loss, the bigger the challenge to the oral microbiota that finds flatter and altered dental surfaces to attach to. In advanced cases of tooth wear, interproximal areas follow the disappearance of all occlusal surfaces with the loss of specific microbiota habitats. Mastication is impaired finally with a shift towards softer diets with further loss of teeth and more profound oral dysbiosis an example of the dysbiosis vicious circle described by the inventors.

The fight against any form of dental plaque or dental biofilm by means of biocides disinfectants, chemical or physical debridement has not proven effective in eradicating periodontal conditions like gingivitis or periodontitis and caries behind premature tooth loss. The increasing number of patients treated with dental implants has given rise to a new condition called Periimplantitis. Implants lacking thick mucosa barrier placed in sites of non-keratinized gingiva exhibit a potential for a specific periimplantitis dysbiosis that cannot be prevented nor treated with antibiotics. Patients wearing prosthesis or dental restorations and the rapidly growing group of patients under orthodontic treatment may also suffer from oral dysbiosis as a result of an imbalanced microbiome consequence of the habitat change imposed by artificial materials.

As well as in the oral cavity, skin is home to an extense microbiome with specific microbiota for the different skin types and sites. Skin exhibits a high rate of desquamation and cell renovation like mucosa. Depending on the degree of sebaceous or aqueous secretion we can find 3 different types of skin:

Sebaceous areas include the scalp, the forehead, the back, the retroauricular crease and the alar crease.

Moist areas include the axillary vault, inguinal crease, gluteal crease, the sole of the foot, the popliteal fossa and the antecubital fossa.

Dry areas include the forearm, buttock, and various parts of the hand.

Inflammation and ulceration in different grades are the most common signs of skin disease. When skin loses a healthy status, it appears with an impaired barrier function, with cracking and reddening.

Among the daily challenges to the skin, alcohols and detergents from soaps and creams can break the integrity of the epidermal barrier by, amongst other mechanisms, removal of lipids that facilitates the colonization of several detrimental bacteria (*Staphylococcus aureus*). This is the case in Atopic Dermatitis in which during the dermatitis flares the bacterial colonization provokes a shift towards low diversity species incompatible with a healthy skin. A similar situation applies to psoriasis.

There is a connection between some medical conditions and both mucosa and skin microbiome, such as chronic inflammatory conditions and cancer. In chronic inflammatory conditions, like diabetes type II, oral and skin microbiome are not only involved in the etiopathogenesis and course of this complex metabolic condition but diabetes changes the environment of the oral, skin and gut microbiome with increasing evidence of the establishment of a diabetes dysbiosis. Diabetes oral dysbiosis courses with higher caries risk, higher periodontitis prevalence and severity, while diabetes skin dysbiosis courses with foot ulcerations, diminished skin elasticity, decreased sebaceous gland activity and less lipid mantum.

Moreover, skin and oral microbiome have been linked to cancerogenic changes leading to melanoma, and oral carcinoma. On the other side of the scale, cancer dysbiosis happens as a result of living with cancer. This cancer dysbiosis reunites a cohort of signs and symptoms with low morbidity but high negative impact on quality of life. Cancer oral dysbiosis courses or is characterized by, amongst others, one, some or all of sore mouth, dysgeusia (altered flavors), high fracture rate, high caries rate, cheilitis angularis (fissures on the angles of the lips), pain in the mouth, and even impairment to eat and have in the skin, a surprising similarity. Cancer skin dysbiosis courses or is characterized by, amongst others, one, some or all of sore skin, altered tact, high fissure rate, ungueitis, pain, and functionally impairment related to skin of the distal parts of the body mainly hands and feet but also the skin of the back, legs and torsum.

The oral mucosa, as any mucosa of the body, is, in many ways, similar to skin. Oral mucosa consists of two distinct layers: the stratified squamous epithelium and the lamina propria. In some places of the oral cavity, the oral mucosa is attached to underlying structures by a loose connective tissue component, the submucosa. These three layers are analogous to the epidermal, dermal and hypodermal layers of skin (see FIG. 1). In fact, pathologies such as Lichen Planus and Pemphigus affect both skin and oral mucosa. Thus, in the present invention they are embodiments of both oral dysbiosis and skin dysbiosis.

Lung dysbiosis follows the disruption of the lung microbiome that loses homeostasis and starts a dysbiosis. The most common initiators in the lung dysbiosis are environmental changes such as dehydration, desiccation by oxygen therapy, change of temperature, pH change, tobacco, tobacco substitutes (vaping), lifestyle habits, alcohol, diet, pollution, radiation, oxygen gradient, intake of medications, diseases such as cancer, infections and diabetes, obesity, and ageing, between others. Interestingly, a decrease in diversity and specificity of the microbiome of the different microenvironments within the body is found in the elderly populations, explaining the increased fragility in ageing associated to the loss of species richness.

Lung dysbiosis can also happen as a consequence of mucosa penetration of bacteria, virus or fungi that encounter a microbiota with decreased diversity. Whether the microbiome changes are a cause or a consequence of the development of a pneumonia, for instance, or merely coincides or is associated with disease status, remains a question of debate. However, in view of the current investigators, the microbiome vicious circle and the perpetuation of the dysbiosis in disease and disease in dysbiosis described as Microbiome Dynamics Model of Eubiosis and Dysbiosis in the current invention explains why lung health is the outcome of a complex interaction between the host and the microbiome.

Bearing all the above in mind, in a particular embodiment of any aspect of the invention, "oral dysbiosis" includes, but is not limited to, halitosis dysbiosis, caries dysbiosis, periodontal dysbiosis, aphthous dysbiosis, periimplantitis dysbiosis, Lichen Planus dysbiosis, Pemphigus dysbiosis, sleep apnea dysbiosis, stress dysbiosis, tooth wear dysbiosis, diabetes oral dysbiosis, cancer oral dysbiosis and combinations thereof. Preferably, oral dysbiosis is selected from caries dysbiosis, tooth wear dysbiosis, periodontal dysbiosis, aphthous dysbiosis, periimplantitis dysbiosis, sleep apnea dysbiosis, diabetes oral dysbiosis, cancer oral dysbiosis and combinations thereof.

Likewise, in a particular embodiment of any aspect of the invention, "skin dysbiosis" includes, but is not limited to, atopic dermatitis dysbiosis, acne vulgaris dysbiosis, psoriasis dysbiosis, xeroderma dysbiosis, skin allergies dysbiosis, radiodermatitis dysbiosis, solar dermatitis dysbiosis, contact dermatitis dysbiosis, seborrheic dermatitis dysbiosis, scalp dysbiosis (dandruff, alopecia), body malodor dysbiosis (armpit, feet), premature skin aging dysbiosis, Lichen Planus dysbiosis, Pemphigus dysbiosis, and combinations thereof. Preferably, skin dysbiosis is selected from atopic dermatitis dysbiosis, acne vulgaris dysbiosis, psoriasis dysbiosis, xeroderma dysbiosis, body malodour dysbiosis, premature skin aging dysbiosis, scalp dysbiosis and combinations thereof.

In a particular embodiment of any aspect of the invention, "lung dysbiosis" includes, but is not limited to, chronic pulmonary dysbiosis, chronic obstructive pulmonary dysbiosis (COPD), cystic fibrosis dysbiosis, asthma dysbiosis, tracheitis dysbiosis, bronchitis dysbiosis, and respiratory infectious dysbiosis.

In a particular embodiment, the respiratory infection is a lower respiratory infection due to bacteria colonization (e.g. *Streptococcus*), virus colonization (e.g. influenza, parainfluenza, coronavirus, coronavirus SARS-CoV-2, syncytial respiratory virus) or fungi colonization (e.g. *Candida, Pneumocystis*). More particularly, the respiratory infection is selected from de group consisting of cold, pneumonia, influenza and coronavirus SARS-CoV-2 disease (Covid-19). Thus, in a particular embodiment according to the invention, the lung dysbiosis is cold dysbiosis, pneumonia dysbiosis, influenza dysbiosis or coronavirus SARS-CoV-2 dysbiosis.

In a particular embodiment of the present invention, oral dysbiosis is assessed by clinical parameters (signs and symptoms) such as: gum bleeding upon interdental brushing, tooth sensitivity, presence of inflamed gums or inflamed papillae, malodor associated to dysbiosis, discoloration of teeth, tooth wear (erosion, attrition, bruxism) and/or caries, mucosa desquamation, mucosa dehydration, ulceration, aphthous ulcers, pain, dysgeusia (change or absence of taste), lack of elasticity, periimplantitis. Likewise, skin dysbiosis is assessed by clinical parameters such as: dryness of the skin, itching, redness, desquamation, ulceration, pain, bleeding, lack of elasticity, lack of tactile sensitivity (altered or absence of tact), vesicles or ampules after sun exposure.

In another particular embodiment of the present invention, lung dysbiosis is assessed by clinical parameters such as sputum, rhinorrhea, congestion, conjunctivitis, headache, myalgia, aches and pains, cough, dryness, sore throat, roughness, coarse voice, dysgeusia-ageusia, anosmia, impaired oxygenation level, chest pain or pressure, shortness of breath, difficulty in breathing or/and fever.

The complex Covid-19 is yet an unknown entity both in its origin and its treatment. However, increasing evidence of the role of an altered microbiome in the course of the disease offers a new perspective both for the prevention and treatment. The decrease found in bacterial diversity in Covid-19 patients when compared to healthy subjects, together with the fact that a parallel and simultaneous reestablishment of upper respiratory and gut microbiomes take place in most of mild Covid-19 patients support the theory of a dysbiosis associated to coronavirus disease that affects beyond the lung. Furthermore, the decreased diversity in most of the microbiome environments in older individuals inherent to ageing might eventually explain the rapidly severe progression of Covid-19 and high rate of fatal outcome. In the view of the current investigators coronavirus dysbiosis takes advantage of a disruption of the microbiome that trespasses mucosa of the lung onto other mucosas like digestive but also to skin, being a particular example of an oral-lung-gut-skin axis. In fact, symptoms and signs associated to coronavirus dysbiosis appear in the mouth, in the lung and upper respiratory tract, in the digestive system and in the skin, being the list of symptoms and signs continuously updated. In any case, in the present invention Covid-19 dysbiosis is considered a particular embodiment of lung dysbiosis since originally it was described as a respiratory infection.

Attending to the order listed before the signs and symptoms of coronavirus dysbiosis are in the mouth, dryness of the mucosa (dry mouth), loss or absence of taste (dysgeusia or ageusia), vesiculobullous lesions, aphthous-like lesions, loss or absence of smell (anosmia). In the upper respiratory tract and lung, dryness of respiratory mucosa (dry cough), voice alteration, sore throat, difficulty in breathing and shortness of breath. In the gut, diarrhea, in skin, skin rush, discolouration of fingers and toes.

In a first aspect, the present invention refers to a composition comprising an olive product, betaine and xylitol (hereinafter referred to as composition of the invention) for use in the prevention and/or treatment of dysbiosis. In light of Example 7, it also refers to the composition of the invention for use as adjuvant in the prevention and/or treatment of dysbiosis.

Compositions comprising an olive product, e.g. olive oil, betaine and xylitol are already known in the state of the art, see for example EP 2119477 A1 and WO 2019/025366 A1, but for other unrelated uses. In particular, EP 2119477's composition can be used for the treatment of xerostomia. Nothing in the state of the art suggests that a proper salivary function would prevent dysbiosis from occurring, nor that xerostomia free patients would be dysbiosis-risk free. A sufficient salivary production is not a warranty of eubiosis, otherwise caries, periodontitis and other oral dysbiosis would be prevented with a normal salivary flow. In fact, nothing has been written about the preventive action of salivary flow in the most prevalent oral dysbiosis that is periodontitis and vice versa, patients with xerostomia do not exhibit a higher risk of periodontitis. Similarly, patients suffering from Eating Disorders or from Gastro Esophageal Reflux Disorders experience a compensatory overflow of saliva and yet suffer an easy to recognize Tooth Wear Oral Dysbiosis consisting of a disruption of the dental biofilm first of the lingual aspect of teeth, second occlusal surfaces (masticatory surface) and finally buccal. Teeth are eventually deprived of all lipophilic content loosing the barrier effect that this dental biofilm should perform and destroying teeth that cannot be salvaged by means of mouthguards of any sort.

WO 2019/025366 A1's composition can be used for the treatment of Oncologic Treatment Induced Orogastrointestinal Mucositis (OTIOM), a life-threatening condition for cancer patients undergoing treatment with either chemo and or radiotherapy. This OTIOM differs from oral and skin dysbiosis in the sense that it is self-limiting, it does not affect skin nor teeth, and it is not linked to the microbiome nor a pathogen of any origin. It is a toxic acute disruption of the orogastrointestinal mucosa that is the single most feared complication of cancer therapy and that is not treated with antibiotics neither probiotics nor prebiotics. In fact, probiotics are absolutely contraindicated during OTIOM for the high risk of sepsis.

Interestingly, as shown in the Examples, the composition of the present invention, comprising an olive product, betaine and xylitol, has a new medical use as it is useful for the prevention and/or treatment of dysbiosis. Surprisingly, compositions comprising an olive product, betaine and xylitol show an unexpected synergistic effect over compositions comprising only one of said ingredients or a combination of an olive product and betaine (see Examples 1, 3, 4 and 8). Moreover, the different Examples show the utility of the composition of the invention for the treatment and/or prevention of both mucosa dysbiosis and skin dysbiosis.

The particular and preferred embodiments of the dysbiosis are the ones described above and applicable to all the aspects of the invention.

In a particular embodiment according to the first aspect of the invention, the olive product is selected from olive oil, olive fruit extract and mixtures thereof. The olive fruit extract can be an olive fruit liquid extract (also known as olive fruit fluid extract), an olive fruit dry extract (also known as olive fruit dry powder extract) or a mixture thereof. Preferably the olive fruit extract is an olive fruit liquid extract and an olive fruit dry extract.

Olive fruit extracts are known by the skilled in the art and commercially available. Likewise, methods of extraction from the olive fruit are well known. Examples of said methods are disclosed in WO2008142178A1 and ES2051238A1. In a particular embodiment, the olive fruit extract is an olive fruit extract rich in hydroxytyrosol. More particularly, the olive fruit extract comprises at least 20% (w/w) of hydroxytyrosol. Examples of these extract are available by Nutexa Inc and Natac, amongst others. Preferably, the olive product is olive oil, more preferably the olive oil is selected from the group consisting of extra virgin olive oil, virgin olive oil, and even more preferably the olive oil is extra virgin olive oil (EVOO), which as shown in the Examples has outstanding effects in treating and preventing dysbiosis.

Betaine can be used in any of its presentations, either as aqueous solutions or powder. In a particular embodiment according to any one of the preceding embodiments, betaine is selected from the group consisting of trimethylglycine (TMG), cocamidopropyl betaine, dimethylamine betaine, alkyl ($C_{12}$-$C_{18}$) amido betaines, alkyl ($C_8$-$C_{18}$) betaines, amidobetaines, alkyl amido betaines, sulpho hydroxy betaines and combinations thereof, preferably betaine is trimethylglycine, which as shown in the Examples has outstanding effects in treating and preventing dysbiosis. More preferably, trimethylglycine is chosen for the formulations for the mucosa and skin.

Olive oil is used in food industry as a preservant for its antibacterial, antifungical, antivirical properties. It has been published as irritant with a pungent flavor, and even barrier disrupting effect on stratum corneum integrity by means of increased Trans epidermal water loss (TEWL) after topical application to the skin in subjects with and without Atopic Dermatitis. In skin, olive oil has been claimed to cause contact dermatitis and to have anti-inflammatory benefits but also irritant side effects with barrier disruption consequences. Betaines, commonly used in mouthwashes, for its antiseptic activity, have the risk to disturb the healthy balance of the biofilm when used over 2 weeks. Xylitol is a well-known anticariogenic ingredient more and more commonly introduced to consumers. Xylitol has documented anti *Streptococcus* activity specially when used as a remineralizing agent by itself. However, a recent study benefiting from the latest computational science using rRNA gene sequencing, has investigated the impact of xylitol on the composition of the oral microbiota showing no evidence after the use of either xylitol or sorbitol on previously documented caries associated nor caries protective species. This is a new piece of controversy about xylitol's dental benefits. Interestingly, when included in oral hygiene compositions, if it is accompanied by other minerals and salts with remineralizing potential a proven decrease in the anti-plaque effect of xylitol has been found. Despite the possible beneficial effect of xylitol for humans (highly toxic for animals) when orally consumed in high percentage or for a long time, the digestive alterations that follow (bloating, diarrhea) might be a marker of the undesirable gut microbiome imbalance that returns to homeostasis upon cessation of intake (Storey, Lee, & Bornet, 2007). In skin dysbiosis and/or vagina dysbiosis (vaginosis) high concentrations of xylitol is non desirable neither as it could shift phyla of the type Bacilli (Lactobacilli) and Streptococci and Staphylococci. Surprisingly, the composition of the present invention does not show any of these detrimental effects. In fact, the composition of the present invention retains hydrophilic bacteria and lipophilic bacteria, without exerting the antimicrobial properties of olive oil, betaine and xylitol when by themselves. The composition of the invention has proven to be effective in preventing dysbiosis in the mucosa and the skin, when applied topically by forming a 3D structure that helps to maintain the proprietary microbiota when hazards appear.

The composition of the invention provides a three-dimensional amphipathic scaffold that incorporates water also from the atmosphere hydrating the ecosystem of the microbiome and at the same time hydrating the skin and mucosa of the human being, ultimately providing protection from external offences (deprivation of humidity, pH shifts, temperature oscillation, antiseptics, detergents, radiation, between others), restriction to the penetration of detrimental agents and house to the necessary for cell life, that is water and nutrients.

Microbiome ecosystem is enhanced by the composition of the invention, as it is improved for a better attachment of the resident microbiota by the hydrophobicity of olive oil, the moisture retention of betaine, and the humectant effect of xylitol, which capture moisture from the atmosphere, a more sustainable moisturizer than a mere solution in water or a dual phase solution. In fact, an emulsion of olive oil in the absence of betaine and xylitol is not able to provide the humectant moisture effect desired both in the skin and the mucosa.

The concept of epithelial homeostasis explains that there is a continuous replacement of cells with desquamation of the more superficial cells with a positive effect limiting microbial colonization and a negative effect as the resident microbiota is partially lost. However, these living microbes need their ecosystem to install themselves.

Researchers have intended to identify the good bacteria behind health and on the contrary the populations behind disease. Unfortunately, this simplification has proven wrong as the same bacterial types are found in the diseased and the controls, but in a different proportion. It has not yet been able to conclude that the microbiota shift is the origin of the disease itself. An associative more than a causative relation is speculated while the latter prevails in infectious conditions. In other words, a certain microbiota of an illness seems to be associated to more than originated from such a condition.

In nature, ecological changes start in the habitat and then either adaptation or disappearance of certain species occur. Trying to maintain a stable microbiome by acting through the microbiota has had so far controversial results. The inventors of the current invention regard the ecosystem as the first recipient of damage. This in term is responsible for the microbiota shift which is in itself a cause of environmental changes. This is represented in what the inventors define as the Microbiome Dynamics Model of Eubiosis and Dysbiosis (FIG. 2).

Human evolution has resulted in primary symbiosis or eubiosis with health being normality. However, when dysbiosis appears, the asymbiotic microbial population together with an altered ecosystem perpetuates the vicious circle like in obesity or depression both entities understood today in relation to dysbiotic microbiome and with a frustrating reluctancy both to diet and psychotherapy.

Our body faces daily offenses, in particular stress, pollution, hyper connectivity, WIFI, chemicals, antiseptics, antibiotics, drugs, detergents, radiation, oxidative stress, infectious agents, fast food, oral and skin hygiene, shampoos, feminine hygiene, wounds, eating disorders, mouth breathing, sleep apnea, systemic and chronic conditions that have an impact in our microbiome.

Certain individuals lack the necessary inner or outer conditions to repair the microbiome and hence develop disease. Once the microbiota has shifted the rehabilitation of the healthy population of bacteria needs a healthy promoter that can act directly on the microbiota, or indirectly on the environment. Surprisingly, the composition of the present invention is able to restore and promote healthy microbiota and its ecosystem through enhancing the support for the ecosystem of a healthy environment. The approach of the current inventors is towards enhancing the environmental conditions and ecosystem that favor the maintenance and re-establishment of a healthy microbiota, whichever the site. The composition enhances the compartment of the resident microbiota as it has yet been impossible to identify the microbes, one or several, with a causative relation with most of the conditions and diseases studied so far. Improving human microbiome through the ecosystem compartment is less site specific as shown in the Examples. This mechanism is represented in a schematic way in FIG. 3.

In a particular embodiment according to any one of the previous embodiments, the composition does not comprise any other vegetable oil, more particularly, it does not comprise parsley oil. Like this, the use of oils of lower quality, e.g. palm oil, is avoided. The composition can, however, comprise essential oils, thus, in a particular embodiment the composition does not comprise any other vegetable oil, except essential oils.

In a particular embodiment according to any one of the preceding embodiments, the composition comprises 0.05%-5.1% by weight of olive product, preferably 0.05%-4.1% and more preferably 0.05-2.6% of olive product. Preferably, when the olive product comprises or is an olive fruit extract, the composition comprises 0.05%-0.1% of olive fruit extract, and when the olive product comprises or is olive oil, the composition comprises 0.1%-5%, more preferably 0.1%-4% and even more preferably 0.2%-2.5% of olive oil.

In another particular embodiment according to any one of the preceding embodiments, the composition comprises 0.1%-10% by weight of betaine, preferably 1.0%-6% and more preferably 1.20%-5%.

In another particular embodiment according to any one of the preceding embodiments, the composition comprises xylitol, preferably 1%-20% by weight of xylitol, more preferably 1%-15%. Advantageously, in smaller concentrations (e.g. ≤20%), xylitol acts as moisturizer and refresher helping to improve the prevention and treatment of dysbiosis.

All the percentages given in the present invention are given in weight by weight of the total composition (w/w), unless otherwise stated.

As shown in the Examples, compositions comprising an amount of olive product, betaine and xylitol within the ranges defined above are very effective in the treatment and prevention of dysbiosis. In another preferred embodiment, the composition of the invention comprises the olive product, betaine and xylitol in the amounts defined in any one of the formulations described in the Examples.

In a particular embodiment according to any one of the preceding embodiments, the composition comprises an antioxidant and/or vitamins. Preferably, the antioxidant is a natural antioxidant, more preferably an antioxidant from *Olea europeae*. Preferably, the antioxidant is selected from the group of hydroxytyrosol, tyrosol, oleuropein, and mixtures thereof. Interestingly, hydroxytyrosol, tyrosol and oleuropein potentiate the anti-inflammatory and antioxidant activities of the olive oil and appear to be able to stabilize the composition (i.e. reducing, or even eliminating, the need of further preservatives which will make the formulation more tolerable by the subjects). Thus, in a preferred embodiment the composition comprises hydroxytyrosol and/or tyrosol and/or oleuropein, preferably it comprises hydroxytyrosol, tyrosol and oleuropein.

According to the desired presentation/formulation, the composition includes all those components necessary to provide the desired organoleptic and rheologic form. Thus, in a particular embodiment according to any one of the preceding embodiments, the composition further comprises one or more components selected from the group consisting of: remineralising agents, viscosity-controlling agents, moisturising agents, preservatives, colorants, pH-regulating agents (buffer), sweeteners, emulsifiers, proteolytic enzymes, whitening agents, probiotics, abrasives, essential oils, cicatrizing agents, aromas, animal or plant gelatins, rheological agent, solvent, excipients and combinations thereof.

These further components of the composition of the invention are commonly known by the skilled in the art, and non-limiting examples of said compounds are given below. In a particular embodiment according to any one of the preceding embodiments, these compounds are selected from the following examples. The remineralising agent can be chosen among fluoride anions, phosphate anions, calcium cations, potassium cations and mixtures thereof. The rheologic agent can be selected from the group consisting of arabic gum, tragacanth gum, xanthan gum, carboxymethyl cellulose, carbopol-type polymers, pectins, mucines and mixtures thereof. The moisturizing agent can be selected from the group consisting of glycerin, propylene glycol, sorbitol and mixtures thereof, preferably glycerin. The preservatives can be selected from the group consisting of sodium benzoate, potassium sorbate, benzoic acid, diazolidinyl urea, imidazolinyl urea, sodium methylparaben, sodium propylparaben, and mixtures thereof. The sweetener can be selected from the group consisting of maltitol, isomaltitol, manitol, lactitol, sodium saccharine, acesulfame potassium, aspartame, cyclamate, taumatin, sucralose, *Stevia rebaudiana*, neohesperidine DC and mixtures thereof. The emulsifier can be selected from the group consisting of polyethylene glycol (PEG) 40 hydrogenated castor oil, lecithin and mixtures thereof.

Recent studies have proven a relationship between the use of biocides in toothpastes for general use and the multiple and serious direct side effects on distant parts of the body. A multicentric university animal study proved that triclosan, widely used in oral care products, was detected in blood upon application in the oral cavity and directly related to several pathologic conditions like colitis, inflammatory changes of the gut, between others, and the most common form of cancer, colon cancer (Yang, Wang, & Romano, 2018). The authors of the study recognize the animal-human translational particularities but alert the medical and health authorities and professionals as they outline that the results obtained in the study have happened after a small exposure to triclosan and human beings widely use it for oral hygiene, three times a day for long-life periods of time.

Antifungal agents, even though proven effective for treating dandruff, are not able to stop recolonization from yeast after some weeks. However, the composition of the present invention is able to enhance the microbial balance by providing the necessary conditions for the scalp microhabitat that will help to stop predominant colonization from pathogenic microbes like yeast from *Malassezia* genus.

Thus, in a particular embodiment according to any of the previous embodiments, the composition of the invention does not comprise any additional active principle (e.g. antibiotics, antifungals). In particular, it does not comprise triclosan.

The composition of the invention provides the ideal-physicochemical conditions (pH, barrier integrity and nutrients) that help the healthy balanced microbiota to be maintained and restored in skin and mucosa. Every ecological niche has its own conditions defined by, between others, pH (table 1). Depending on the site of the body, pH will be adjusted to respect the particularities within the body. pH will be adjusted by buffers. Thus, in a particular embodiment, the composition of the invention comprises a buffer. In the composition of the invention any buffer known in the state of the art can be used. In particular, the buffer can be selected from the group consisting of lactic acid, lactates, citric acid, citrates, malic acid and salts thereof, sodium hydroxide, potassium phosphates, sodium phosphates, potassium pyrophosphate, sodium pyrophosphates and mixtures thereof.

TABLE 1

| Area | pH |
|---|---|
| Vagina | 3.8-4.5 |
| Skin of volar forearm | 4.7 |
| Scalp | 4.80 |
| Forehead | 4.80 |
| Lips | 6.61 |
| Tongue | 6.65 |
| Buccal | 6.68 |
| Palate | 7.23 |
| Lung | 6.6 |

Surprisingly, the composition of the present invention maintains its beneficial effects whatever the pH necessary for the different skin and/or mucosa locations.

The skilled in the art can formulate the composition of the invention in any suitable presentation that allows a simple use for the prevention and/or treatment of dysbiosis. In a particular embodiment according to any one of the preceding embodiments, the composition is formulated as facial and/or body moisturizer, deodorant cream, regenerative barrier cream, body gel, shampoo, hair conditioner, hair lotion, skin ampoules, tonic, capsule, tablet, spray, gel, lubricant gel, topical vulvar gel, nasal inhaler, nasal spray, aerosol solution, aerosol spray, aerosol capsules, toothpaste, mouthwash, chewing gum, chewable tablet, suckable capsules, suckable lozenges, palate sheets, sweets, impregnated oral swabs, impregnated oral gauzes, lipstick, balm.

In a preferred embodiment a gel is formed by using gelling agents such as agar, alginate, carrageenan, guar gum, pectates, tragacant gum, carbomers, polymers and silica.

Dry olive fruit extract is preferred for the formulation of lozenges or pastilles, while olive oil, preferably EVOO, and liquid or dry fruit extract are the preferred source of olive product for the formulations of gels, toothpastes, mouthwashes, shampoos, conditioner, hair lotions, creams, masks, lipsticks, sprays, serums, deodorants, capsules, ovules, shower gels. Treatment of Aphthous Oral Dysbiosis has a preferred embodiment in the form of a gel with EVOO as the source of olive product and with hydroxytyrosol for its potent antioxidant action with olive fruit flavor (without stinging flavors). Recurrent aphthous ulcers (RAU) benefit from a preventive hygiene using the same approach in the form of a toothpaste that can also have remineralising agent, natural non-irritating flavors, vitamins, and the necessary for a pleasant hygiene. Patients with Inflammatory Bowel Disease (IBD) or Crohn or gluten intolerance also suffer from aphthous dysbiosis and are candidates for the same measures. In the Stress & tooth wear Oral Dysbiosis and in the Sleep Apnea Oral Dysbiosis as well as Oral Dysbiosis associated to eating disorders or gastric reflux a gel is ideally formulated to be applied topically into the oral tissues several times per day after oral hygiene and specifically before bed time and upon awakening.

The administration of the composition of the invention for preventing or treating lung dysbiosis can be done by any known administration route. Not limiting examples are liquid presentations for nasal inhaler, nasal spray, nasal aerosol, nasal gel, oropharyngeal syrup and oropharyngeal gel and solid presentations as aerosol capsules. The composition of the invention can be included in care and hygiene products for different skin and mucosa areas.

"Care" refers to the recovery, improvement or protection of the mucosa and skin microbiota necessary whenever a hazard risks the natural and healthy microbiome (i.e. hygiene with caustic products or alcohol, detergents, etc.).

"Hygiene" refers to the act through which we eliminate excess of residual cells and other substances naturally produced susceptible to provoke a disturbance of the natural and healthy microbiome.

Different formulations and vehicles and/or excipients should be used depending on the body area in/on which the composition is to be applied. The skilled in the art knows how to adapt each composition for each body area, depending on, amongst others, the pH of the tissue and other particular physicochemical properties of the tissue.

For instance, some areas of the skin are more sebaceous, moister or drier than others. Care and hygiene products would be adapted to this property.

In the same sense, different products would be adapted to the different mucosa, as the one in the mouth or the one in the vagina are very different to each other. In a particular embodiment, when detergents are included for hygiene, the composition of the invention continues to deliver the beneficial effects for the ecosystem and restore eubiosis as seen in the examples. In presentations including whitening ingredients, either for teeth or skin, the composition of the invention also exerts its microbiome beneficial activity reducing the possible irritative, desquamative or sensitivity effects of the whitening principles.

Along the human body the microbiota is adapted to the different habitats with some particularities. In accordance to the Human Microbiome Project there are different microbial communities between 10 different particular sites within the digestive tract such as buccal, gingival and hard palate (group 1) and saliva, tongue, tonsils and throat (group 2) (Segata, Kinder Haake, & Mannon, 2012). This topographic variation is surprisingly higher than between different individuals. Similarly, skin has sebaceous sites (scalp, back, forearms) and moist locations with site specific microbiota that as well as oral mucosa have also temporal variations but for most of time remains stable throughout long periods. Topographic and temporal behaviour and richness or abundance are today being studied. Similarities in the fact that lipophilic bacteria in the oral cavity reside predominantly in the hard palate, the lingual aspect of the teeth, the keratinized gingiva and buccal mucosa have been found. As seen by the authors of the present invention, not only these bacteria show more resistance to the digestive acids and to bolus passage but they also generate fatty acids through metabolizing triglycerides that bathe the rest of the oral cavity with a lipid mantum that serves as protection, lubrication and helps to perpetuate the lipidic component of the oral biofilm. In the same manner the inventors of the current invention propose a positive enhancement of this natural lipophilic protection with the current composition.

Whether high in diversity (oral mucosa) or low (scalp, back and forearms, or vagina), this biofilm seems to perform valuable functions like immune defence, nutrition, metabolic, even growth and personality of the beholder when behaving in a symbiotic way (healthy). It remains still unclear when and why it shifts to dysbiotic (disease) per a yet undiscovered trigger may it be a keystone pathogen or a major environmental challenge like stress or more strikingly hygiene as stated before.

The microbiota is in constant movement and renovation and at the same time shows a resilience to change. Identifying the core microbiome of a certain anatomical site or the key pathogen of a specific dysbiosis remains a phenomenal task despite of the advent of next-generation sequencing that provides less bias than previous culture-based technologies. This is the case of periodontitis, an oral dysbiosis that accounts for the most highly prevalent disease among the world population. For many years periodontologists evolved from believing gram negative bacteria were responsible for periodontitis to accepting gram positive and gram negative being behind the shift from initial gingivitis to evolved periodontitis with the occurrence not truly causative but associative of bacteria adapted to oxygen deprivation (anaerobic) and hemo dependent ("red complex" bacteria; *Treponema denticola, Tannerella forsythia* and *Porphyromonas gingivalis*) profiting from what was originally thought to be a secondary inflammation. To make things more complex it is yet ignored whether if *P. gingivalis*, widely recognized as the landmark pathogen in periodontitis, starts an inflammatory response by shifting the normal commensal microbiota that, then, terms dysbiotic, or if even in low abundance condition this pathogen has a symbiotic deleterious behaviour with dormant so called fastidious microbes that only recently have been identified. This is the case of *Filifactor alocis*, which seems to be involved in major oral dysbiosis as it is rarely found in healthy individuals. Surprisingly, *F. alocis* is a gram positive asaccharolytic anaerobic bacteria that inhabits subgingival areas with low oxygen gradient and is able to live on short chain fatty acids that when metabolized release ammonium and increase pH to the neutral range. This in terms exclude gram positive oxygen dependent bacteria with acidic metabolism like *Streptococcus mutans*. This is the reason behind patients exhibiting periodontal susceptibility and not caries risk and vice versa. It is not yet known whether if the ability of *F. alocis* to thrive in highly oxidative conditions lead to further oxidative stress environmental changes potentially proclive for other dysbiosis like OLP or cancerogenic changes.

In the imbalanced situation of dysbiosis, the altered microbiota interacts with the human body in a modified environmental atmosphere (temperature, pH, humidity and oxygen conditions) that tends to perpetuate the microbial shift.

Not only microbes are replaced but the ecosystem changes at the same time and this dual shift is clinically detected by means of negative conditions such as inflammation, barrier breakage, bleeding, desquamation, irritation, dehydration, and sometimes infection of the body or eventually cancerogenic changes.

The role of human microbiome in skin and oral dysbiosis like the diseases mentioned here is today stablished through research but suspected before as many of these negative conditions with unknown origin improved with antibiotics (AB). Unfortunately, AB resistance and side effects are common drawbacks. As shown in the Examples the composition of the invention is able to revert these negative conditions and improve health through the ecosystem enhancement finally achieving eubiosis. Thus, in a particular embodiment of the invention according to any of the preceding embodiments, the composition does not comprise antibiotics.

Attempts to increase health through the microbiome have been principally done through trying to modify the microbiota usually adding microbes supposedly beneficial, the so-called probiotics, with controversial results. In any case, the present invention is compatible with pre and probiotics. Thus, in a particular embodiment according to any one of the preceding embodiments, the composition further comprises prebiotics and/or probiotics. In a preferred embodiment, the composition is a suckable lozenge that comprises olive dry fruit extract, betaine, xylitol and probiotics, more preferably it also comprises the necessary ingredients to formulate it as a dry presentation.

The composition of the present invention comprises a lipidic-lipophilic fraction (olive product) that attaches to the tissues for a longer time preventing evaporation and a hydrophilic fraction (betaine and xylitol) that attracts humidity within this scaffold to enable for microbiota interaction with the host and with its ecosystem. Microbiome ecosystem is enhanced by this composition, as it is improved for a better attachment of the resident microbiota.

As shown in the Examples, the composition of the present invention has unprecedented beneficial properties that not only counteract the negative effects of olive oil or betaine used topically but also amplify an unexpected benefit for oral and skin microbiome when applied directly to the skin and mucosa.

Skin and mucosa provide an efficient barrier against pathogens and water loss. Skin and mucosa barrier disruption leads to an inflammatory redness which signifies dilatation of the vessels and increased blood flow. The use of the composition of the invention has demonstrated to reduce inflammation and at the same time to regenerate damaged tissues. It is important to highlight that other inflammatory inhibitors are not able to regenerate the tissue, what makes this composition unique as this property has not been obtained in humans with any other composition (Van Dyke, 2017) (see, e.g., Example 4).

A bacterial selection occurs as a consequence of an altered skin or mucosa. Inflammation of gums increases collagen peptides, plasma proteins and haemoglobin that select specific bacteria characterized by the use of essential amino acids and hemin as nutrients.

The composition of the invention reduces permeability and regenerates tissues, avoiding the release of the nutrients that promotes dysbiosis (collagen peptides, plasma proteins and haemoglobin) thus obtaining a natural and healthy equilibria of the bacteria that populates the tissue. At the same time, avoiding the release of these molecules helps maintain the natural healthy colour of either mucosa, teeth and skin.

In the current invention the composition enhances and does not eliminate the adequate oral and skin biofilm to promote a balanced and diverse microbiota and to maintain and restore the proprietary microbiome respecting the underlying tissues.

Furthermore, the discovery of the composition of the invention treating and preventing oral and skin dysbiosis and enhancing oral and skin homeostasis supports the adequate environment for the oral and skin microbiome without exerting any pressure on commensal microbes that might trigger or propagate a dysbiotic spur.

The composition of the present invention has a lipidic-lipophilic fraction (olive product) that attaches to the tissues for a longer time preventing evaporation and with a hydrophilic fraction (betaine and xylitol) that attracts humidity within this scaffold to enable for microbiota interaction with the host and with its ecosystem. Microbiome ecosystem is enhanced by this composition, as it is improved for a better attachment of the resident microbiota.

To the knowledge of the inventors, nothing in the state of the art has anticipated an Oral-Skin Axis. Gingivitis occurs frequently in patients suffering from Acne Vulgaris. In Acne skin flares, patients experience also gum bleeding and swelling sometimes even before skin breakup. Both conditions happen usually in adolescents but also in children and is not uncommon in adults. Both conditions are related to western diet, stress, and are between the most common reason for visiting the specialists. The severity ranges between open or closed comedones (black head and white head) to clearly inflammatory lesions (pustules even cysts) in acne and inflammation of the gingiva to bleeding and ulceration (ulceronecrotic lesions). The trend today is to consider Acne Vulgaris a skin dysbiosis with a colonization with *Propionibacterium acnes* as an associative agent facilitated by the change in the environment conditions of the skin. In Gingivitis also Gram-positive bacteria are found. However, till now, no pathogen has been identified but similarly to acne, there is an increased reaction from the host interrupting the barrier and permitting colonization. As shown in the Examples, an improvement in the gingiva is related with an improvement of the acne, what is consistent with this newly described Oral-Skin Axis.

Finally, nothing in the state of the art has linked tooth wear with oral dysbiosis, however, in view of the current invention the imbalance in minerals exchange behind the mineral loss in erosive damage can be prevented with the restoration of the appropriate barrier function of the oral microbiota when in balance. As shown in the Examples and explained in the previous arguments, a balanced microbiota in a favourable ecosystem counteracts the acidic challenges and an indirect amelioration of tooth hypersensitivity occurs after using the composition of the present invention. The use of the composition of the invention, in particular in the form of a toothpaste and a mouthwash, prevents the dysbiosis and restores homeostasis. If dysbiosis is present, all these conditions benefit from the topical application of said composition ideally in the form of a gel or a spray to revert to eubiosis in the early onset of dysbiosis.

The Skin-Gut Axis is today the focus of research throughout universities aiming to explain and describe the relation between the gut microbiome and skin health and the so far elusive communication between these apparently non-connected body sites and the translational potential of improving gut microbiome and skin therapies. (Salem, Ramser, Isham, & Ghannoum, 2018) (Lee, Byun, & Kim, 2019) (Vaughn, Notay, Clark, & Sivamani, 2017) (Szántó, Dózsa, & Antal, 2019).

Nothing in the state of the art to the knowledge of the authors of the current invention has been proclaimed about oral microbiome and a systemic effect that happens as a malfunction of the mouth during sleep called Sleep Apnea or Obstructive Sleep Apnea (OSA) and considered by the authors a dysbiosis. Sleep Apnea varies from snoring to true interruptions of respiration in the severe forms that impact negatively on sleep quality with frequent awakenings and poor rest during night. Day time irritability, lack of concentration, day sleep, depression and anxiety together with high cardiovascular risk are experienced by patients and doctors that direct the patients to maxillofacial surgeons and dentists for mandibular advancement therapy invasive or non-invasive (removable mouth splints) as an alternative to sleeping connected to mechanical continuous positive airway pressure known as CPAP. Nothing has been written about the role of oral microbiome in OSA, neither as the origin of the problem nor as a consequence of it. The current invention considers sleep apnea dysbiosis starts in an altered environment similar to what happens in mouth breathers. Intense and persistent changes in the humidity conditions of the mucosa impair the mucosa structural architecture but also the microbiome compartment with a collapsed pathway critical for the inflow of air in OSA. Hydration through sipping water upon awakening is only a short-term solution and forces nocturia. OSA courses with repeated interruption of sleep, poor night rest and day consequences in the social, psychological and health aspects of the individual. The Oral-Brain axis connection has been described as mentioned before and this could well be another example of such connection. Patients using the composition of the invention in the form of spray applied before bedtime and upon awakening during the night show a significant improvement of signs and symptoms associated to sleep apnea dysbiosis such us quality of night rest, day irritability, episodes of night awakening, episodes of water sipping during the night. Patients with CPAP using the composition had better compliance when compared to a water spray.

Finally, as explained above, the composition of the invention serves to prevent and/or treat dysbiosis. Advantageously, as shown in Example 5, it also serves to prevent pathologies facilitated or exacerbated by dysbiosis. Moreover, it can serve for treatment, particularly as adjuvant treatment, of said pathologies. Said pathologies can be exacerbated by dysbiosis because dysbiosis increases the number of episodes of said pathologies or because dysbiosis exacerbates the signs and/or symptoms of said pathologies. The signs and/or symptoms can be exacerbated by dysbiosis in terms of the variety, intensity and/or duration. Thus, the first aspect of the invention refers also to the composition of the invention as described in any of the above-mentioned embodiments for use in the prevention and/or as adjuvant treatment of a pathology facilitated or exacerbated by dysbiosis.

Recent research agrees in considering the disbalance of scalp microbiome as a major contributing factor for conditions such as dandruff or seborrheic dermatitis. There is a connection between some medical conditions and both mucosa and skin microbiome, such as chronic inflammatory conditions and cancer. In fact, skin and oral microbiome have been linked to cancerogenic changes leading to skin cancer (e.g. melanoma), and oral carcinoma.

In the lung, similarly to what happens in any dysbiosis, the loss of beneficial commensal bacteria implies a diminished protection against opportunistic pathogens like bacteria, fungi and virus that upon colonization will perpetuate the dysbiosis. Moreover, at the same time the lung dysbiosis, if present, may exacerbate conditions and diseases of different natures that otherwise would have a common course. The human lung has evolved to prevent penetration of airborne particles and pathogens with the normality being eubiosis and health enjoyed by young people, and other age groups as long as dysbiosis is not present. This is the case of young populations exposed to coronavirus virus that experience an asymptomatic course or mild cold symptoms, as part of a cold dysbiosis and that reverts to homeostasis within days. This young group that usually benefits from eubiosis when confronted with coronavirus Covid-19, for the majority of cases do not suffer a severe form and experiments a mild or even asymptomatic course that does not progress to a true coronavirus disease, whereas, if dysbiosis is present, as happens in the elderly group, the coronavirus penetration will course in a much more severe form (e.g. more severe difficulty in breathing requiring often times hospitalization and the use of oxygen and or ventilation) as a result of the exacerbation caused by the dysbiosis. Coronaviruses are a large family of viruses that are known to cause illness ranging from the common cold to more severe diseases such as Middle East Respiratory Syndrome (MERS) and Severe Acute Respiratory Syndrome (SARS).

Oral, skin and vagina hygiene disrupt and even destroy biofilms degrading the microbiome compartments. A neglected population of more than 300 of different facultative anaerobic bacteria (Streptococcus salivarius, S. mitis, S. aureus, S. epidermidis, Corynebacterium, between others) live in the crypts of the dorsum of the tongue and have the unique property of reducing dietary nitrate to nitrite, the body's natural vasodilator and gastric protection promoter. Surprisingly, the role of the oral microbiome in the blood pressure, platelet function and bone marrow physiology, as well as cerebral blood flow and peripheral artery disease is out of question but strikingly all these beneficial effects disappear when using an antibacterial mouthwash. Dramatically, in healthy subjects with poor green leaves diet using antibacterial mouthwash a significant increase in systolic and diastolic blood pressure clearly related to the reduction in plasma nitrite has found no echo in a mandatory research yet to be done to prove weather if chronic use of an antibacterial mouthwash leads to elevation in blood pressure and a consequently higher cardiovascular risk. Moreover, periodontitis dysbiosis and cardiovascular disease happen often in the same patient that might be using antibacterials in the mouth (Hezel & Weitzberg, 2015).

Thus, amongst others, the pathology facilitated or exacerbated by dysbiosis can be selected from the group consisting of dandruff, seborrheic dermatitis, chronic inflammatory pathologies, skin cancer (e.g. melanoma), oral carcinoma, and respiratory infections. The later can be bacterial infections (e.g. by *Streptococcus*), viral infections (e.g. by influenza, parainfluenza, coronavirus, coronavirus SARS-CoV-2, syncytial respiratory virus) or fungal infections (e.g. by *Candida, Pneumocystis*).

In a preferred embodiment, the pathology facilitated or exacerbated by dysbiosis is a respiratory infection. More preferably, the respiratory infection is cold, Covid-19 or pneumonia. As shown in Example 5, the use of the composition of the invention surprisingly prevents colds as it reduces the number of cold episodes.

A second aspect of the present invention refers to the use of a composition comprising an olive product, betaine and xylitol for the preparation of a medicament for the prevention and/or treatment of dysbiosis, wherein the olive product is olive oil and/or olive fruit extract. Likewise, it refers to the use of a composition comprising an olive product, betaine and xylitol for the preparation of a medicament for the prevention of a pathology facilitated or exacerbated by dysbiosis or for the preparation of an adjuvant for the treatment of a pathology facilitated or exacerbated by dysbiosis.

A third aspect of the present invention refers to a method of treating dysbiosis or a pathology facilitated or exacerbated by dysbiosis in a subject in need thereof, comprising administering to the subject a therapeutically effective amount of a composition comprising an olive product, betaine and xylitol, wherein the olive product is olive oil and/or olive fruit extract.

A fourth aspect of the present invention refers to a method of preventing dysbiosis in a subject which comprises administering to the subject a prophylactically effective amount of a composition comprising an olive product, betaine and xylitol, wherein the olive product is olive oil and/or olive fruit extract. Likewise, it refers to a method of preventing a pathology facilitated or exacerbated by dysbiosis in a subject which comprises administering to the subject a prophylactically effective amount of a composition comprising an olive product, betaine and xylitol, wherein the olive product is olive oil and/or olive fruit extract.

Finally, recent publications have proclaimed oral hygiene to be the first and the foremost cause for dysbiosis of oral microbiome (Sudhakara, Gupta, & Bhardwaj, 2018). The same has been stated by skin researchers for skin hygiene and skin dysbiosis using a decrease in biodiversity as a marker of skin health deprivation and demonstrating the effect of synthetic ingredients in every day cosmetics (Wallen-Russell, 2019). Thus, a fifth aspect of the present invention refers to the use of the composition as defined in any of the embodiments of the first aspect of the invention for the hygiene of the oral cavity, nasal cavity, vagina and/or the skin of the human body and to the composition as defined in any of the embodiments of the first aspect of the invention for use in the hygiene of the oral cavity, nasal cavity, vagina and/or the skin of the human body, and/or for use in maintaining natural hydration of the mucosa or the skin of the human body. Likewise, it also refers to a method for hygiene of the oral cavity, nasal cavity, vagina and/or skin of the human body comprising the administration of a composition as defined in any of the embodiments of the first aspect of the invention. Likewise, it is also object of the present invention the use of the composition as defined in any of the embodiments of the first aspect of the invention to maintain natural hydration of the mucosa and/or skin of the human body, and a composition as defined in any of the embodiments of the first aspect of the invention for use in maintaining natural hydration of the mucosa and/or skin of the human body. Likewise, it is also object of the present invention a method for maintaining natural hydration of the mucosa and/or skin of the human body comprising the administration of a composition as defined in any of the embodiments of the first aspect of the invention. Preferably the administration is made topically. Preferably, the mucosa is oral mucosa.

The particular and preferred embodiments of the composition of the invention, the dysbiosis and the pathology facilitated or exacerbated by dysbiosis described for the first aspect of the invention are applicable to the second, third, fourth and fifth aspects of the invention.

In a particular embodiment of the invention according to any one of the embodiments of all the aspects of the invention, the administration protocol of the composition of the invention is the one described in the Examples below.

REFERENCES

Atarashi, K., Wataru, S., & Chengwei, L. (2017). Ectopic colonization of oral bacteria in the intestine drives TH1 cell induction and inflammation. *Science,* 358(6361), 359-365. doi:10.1126/science.aan4526

Dawes, C. (2003). What is the critical pH and Why does a tooth dissolve in acid? *J Can Dent Assoc,* 69(11), 722-724.

Hezel, M., & Weitzberg, E. (2015). The oral microbiome and nitric oxide homeostasis. *Oral Diseases,* 21(7).

Lee, Y. B., Byun, E. J., & Kim, H. S. (2019). Potential Role of the Microbiome in Acne: A Comprehensive Review. *Journal of Clinical Medicine,* 987.

Lira-Junior, R., & Boström, E. (2018). Oral-gut connection: one step closer to an integrated view of the gastrointestinal tract? *Mucosa Immunology,* 11(2), 316-318. doi:10.1038/mi.2017.116

Lussi, A., & Carvalho, T. (2015). The future of fluorides. *Caries Res,* 49, 18-29. doi:10.1159/000380886

Paju, S., & Scannapieco, F. (2007). Oral biofims, periodontitis, and pulmonary infections. *Oral Dis,* 13(6), 508-512. doi:10.1111/j.1601-0825.2007.1410a.x Segata, N., Kinder Haake, S., & Mannon, P. (2012). Composition of the adult digestive tract bacterial microbiome based on seven mouth surfaces, tonsils, throat and stool samples. *Genome Biology,* 13, R42.

Sudhakara, P., Gupta, A., & Bhardwaj, A. (2018). Oral dysbiotic communities and their implications in systemic diseases. *Dent. J,* 6(16). doi:10.3390/dj6020010

Szántó, M., Dózsa, A., & Antal, D. (2019). Targeting the gut-skin axis-Probiotics as new tools for skin disorder management? *Experimental Dermatology,* 1210-1218.

Van Dyke, T. (2017). Pro-resolving Mediators in the Regulation of Periodontal Disease. *Mol Aspect Med,* 58, 21-36. doi:10.1016/j.mam.2017.04.006

Vaughn, A. R., Notay, M., Clark, A. K., & Sivamani, R. K. (2017). Skin-gut axis: The relationship between intestinal bacteria and skin health. *World Journal of Dermatology,* 52-58.

Wallen-Russell, C. (2019). The role of every-day cosmetics in altering the skin microbiome: A study using biodiversity. *Cosmetics,* 6(2). doi:10.3990/cosmetics6010002

Yang, H., Wang, W., & Romano, K. (2018). A common antimicrobial additive increases colonic inflammation and colitis-associated colon tumorigenesis in mice. *Sci Transl Med.* doi:10.1126/scitransmed.aan4116

EXAMPLES

Specific embodiments of the invention that serve to illustrate the invention without limiting the scope thereof are described in detail below.

Example 1.—Periodontal Dysbiosis

In the mouth, periodontal disease is the late result of an oral dysbiosis that is often preceded by inflammation and other changes that due to its high rate of appearance, have been understood as normal. We refer to symptoms like gum bleeding, bad breath, tooth sensitivity and others.

In the following study, dysbiosis signs and symptoms were studied in a population of outpatients with a history of periodontal dysbiosis. Subjects rated the intensity of the complaint in a 0 to 10 scale, at the beginning and after 15 days using the assigned composition.

Several compositions, formulated as toothpaste (Table 2), were applied three times per day as the usual hygiene routine, by means of tooth brushing with a toothbrush for 2 minutes after which a rinse with water was performed. No other oral hygiene measures were performed during the duration of the study except for interdental brushing.

Table 2 shows the qualitative and quantitative composition of each composition (comp). Dysbiosis was analyzed assessing the following signs/symptoms:

1. Gum, papillae inflammation (G, PI).
2. Redness or blotting (R, B).
3. Bleeding upon brushing (BB).
4. Bleeding upon interdental brushing (BIB).
5. Sensitivity (S).
6. Presence of detectable malodor on exhalation by a third person (H).
7. Tooth decolouration (TD).

TABLE 2

| | Comp 1.a (% w/w) | Comp 1.b (% w/w) | Comp 1.c (% w/w) | Comp 1.d (% w/w) |
|---|---|---|---|---|
| Olive oil | 0.5000 | 0.5000 | 0.0000 | 0.0000 |
| TMG | 4.0000 | 4.0000 | 0.0000 | 0.0000 |
| Xylitol | 10.0000 | 0.0000 | 10.0000 | 0.0000 |
| Humectant | 39.7714 | 49.7714 | 45.0000 | 54.2714 |
| Solvent | 19.9000 | 19.9000 | 19.1564 | 19.9000 |
| Abrasive | 18.0000 | 18.0000 | 18.0000 | 18.0000 |
| Mineral source | 3.1000 | 3.1000 | 3.5200 | 3.1000 |
| Colorant | 1.0036 | 1.0036 | 1.0036 | 1.0036 |
| Surfactant | 1.0000 | 1.0000 | 1.0000 | 1.0000 |
| Enzyme | 1.0000 | 1.0000 | 1.0000 | 1.0000 |
| Aroma | 1.1000 | 1.1000 | 1.1000 | 1.1000 |
| Sweetener | 0.1250 | 0.1250 | 0.1200 | 0.1250 |
| Preservative | 0.5000 | 0.5000 | 0.1000 | 0.5000 |
| | 100.0000 | 100.0000 | 100.0000 | 100.0000 |

The results, as the average intensity of gum, papillae inflammation (G, PI), redness or blotting (R, B), bleeding upon brushing (BB), bleeding upon interdental brushing (BIB), sensitivity (S), presence of halitosis (H), tooth decolouration (TD) rated from 0 to 10, of the 5 patients of each group at the beginning of the study (t=0) and after 15 days (t=15) are shown in table 3.

The results, as the average intensity of complaints for the different signs/symptoms, rated from 0 to 10, of 5 patients of each group at the beginning of the study (t=0) and after 15 days (t=15) are shown in Table 3.

TABLE 3

| | Average intensity of Complaints | | | | | | | |
|---|---|---|---|---|---|---|---|---|
| | Comp 1.a | | Comp 1.b | | Comp 1.c | | Comp 1.d | |
| | t = 0 | t = 15 | t = 0 | t = 15 | t = 0 | t = 15 | t = 0 | t = 15 |
| G, PI | 6.8 | 1.8 | 5.4 | 4.2 | 6.4 | 6.2 | 5.0 | 5.0 |
| R, B | 7.2 | 2.2 | 6.2 | 4.4 | 7.2 | 6.8 | 6.8 | 6.6 |
| BB | 7.8 | 1.6 | 6.4 | 4.8 | 7.4 | 6.8 | 6.6 | 6.6 |
| BIB | 7.8 | 2.0 | 7.4 | 5.2 | 8.4 | 7.6 | 6.8 | 6.8 |
| S | 5.4 | 2.0 | 6.2 | 5.6 | 6.2 | 5.8 | 6.6 | 7.0 |
| H | 7.2 | 2.4 | 5.2 | 4.4 | 7.2 | 6.6 | 7.6 | 7.2 |
| TD | 7.0 | 2.4 | 7.0 | 5.8 | 6.8 | 6.6 | 8.0 | 7.6 |

The results, as change in the intensity of the complaints assessed for each composition between t=0 and t=15 days are shown in Table 4.

TABLE 4

| | Change after 15 days | | | | | | | |
|---|---|---|---|---|---|---|---|---|
| | Comp 1.a | | Comp 1.b | | Comp 1.c | | Comp 1.d | |
| | Intens-ity | P | Intens-ity | P | Intens-ity | p | Intens-ity | P |
| G, PI | −5 | <0.01 | −1.2 | 0.2 | −0.2 | 0.82 | 0 | 1 |
| R, B | −5 | <0.01 | −1.8 | 0.04 | −0.4 | 0.47 | −0.2 | 0.83 |
| BB | −6.2 | <0.01 | −1.6 | 0.05 | −0.6 | 0.32 | 0 | 1 |
| BIB | −5.8 | <0.01 | −2.2 | 0.03 | −0.8 | 0.30 | 0 | 1 |
| S | −3.4 | <0.01 | −0.6 | 0.58 | −0.4 | 0.77 | 0.4 | 0.57 |
| H | −4.8 | <0.01 | −0.8 | 0.29 | −0.6 | 0.72 | −0.4 | 0.69 |
| TD | −4.6 | <0.01 | −1.2 | 0.02 | −0.2 | 0.76 | −0.4 | 0.70 |

When all the signs/symptoms were considered together, the average of complaints reduction were 4.97 for composition 1.a, 1.34 for composition 1.b, 0.46 for composition 1.c, and 0.09 for composition 1.d.

Thus, when comparing the complaints reduction of signs and symptoms associated to oral dysbiosis obtained for each composition after 15 days of use, a statistically significant effect is shown with the composition of the invention, comprising olive oil, betaine and xylitol. Surprisingly, an unexpected synergetic effect is obtained for the composition of the invention (1.a) in comparison to the other compositions (1.b-1.d).

An improvement in signs or symptoms means a recovery of a balanced microbiome and so a shift from dysbiosis to eubiosis. Thus, the composition of the invention is able to treat dysbiosis and transforms dysbiosis to eubiosis.

Additionally, in order to measure the association of a detectable presence of the periodontal pathogen *Porphyromonas gingivalis*, patients of groups 1.a and 1.d were asked to continue using the assigned toothpaste for another 15 days. At the end of this period, a periodontal probing with a commerciable available test to detect *P. gingivalis* was performed following the manufacturer's instructions (Perio-POC® by Genspeed Biotech).

Patients were also asked again to answer the same questions as before (intensity of gum, papillae inflammation, redness or blotting, bleeding upon brushing, bleeding upon interdental brushing, sensitivity, presence of halitosis, tooth decolouration) in order to detect any possible relapse of the dysbiosis and as an assessment of eubiosis maintenance. The results of the screening for *P. gingivalis* are seen in Table 5.

TABLE 5

| Percentage of patients with detectable *P. gingivalis* in group 1.a | Percentage of patients with detectable *P. gingivalis* in group 1.d |
| --- | --- |
| 25% | 75% |

Regarding the symptoms and signs of dysbiosis no relapse of eubiosis to dysbiosis was found the group using the composition of the invention while the control group did not improve in any of the symptoms.

The outcome of the maintained use of the composition of the invention in oral periodontal dysbiosis was found to be effective in treating dysbiosis and maintaining eubiosis while in the control group the state of dysbiosis perpetuated the symptoms despite the possible benefits of toothbrushing.

Example 2.—Atopic Dermatitis Dysbiosis

To assess the capacity of the composition of the invention to improve signs and/or symptoms associated with dysbiosis in skin, the composition of the invention was applied in the skin of seven patients diagnosed with Atopic Dermatitis from 6 to 14 years old. Signs and symptoms were assessed by patients before (t=0 days) and 15 days after the application of the product. Subjects marked a vertical line through a 100 mm horizontal line to indicate the intensity of the complaint (Visual Analogue Scale (VAS)).

The composition, formulated as hydrating gel (Table 6), was applied three times per day as the usual hydrating routine, by means of gentle distribution by hand. No other hydrating nor cosmetic cream was applied along the duration of the study.

Signs/Symptoms to be analysed:
1. Sensation of dry skin.
2. Itching
3. Redness
4. Desquamation

TABLE 6

| | Comp 2 (% w/w) |
| --- | --- |
| Olive Oil | 0.50 |
| TMG | 4.00 |
| Xylitol | 10.00 |
| Olive fruit fluid extract | 0.10 |
| Others: Solvent (47.70%), humectant (34.50%), mineral source (1.00%), surfactant (1.00%), gelling agent (0.60%), preservative (0.50%), vitamin (0.10%) | 85.40 |

The results, as the average intensity of complaints of the 7 patients at the beginning of the study (t=0) and after 15 days (t=15) are shown in Table 7 and the % of change is shown in Table 8.

TABLE 7

| | Average Intensity of Complaints (VAS) | |
| --- | --- | --- |
| | t = 0 | t = 15 days |
| Dryness | 60.00 | 25.71 |
| Itching | 65.71 | 42.86 |
| Redness | 40.00 | 24.29 |
| Desquamation | 50.00 | 34.29 |

TABLE 8

| | % of change after 15 days | P |
| --- | --- | --- |
| Dryness | −57.14 | p < 0.01 |
| Itching | −34.78 | p < 0.1 |
| Redness | −39.29 | p = 0.1 |
| Desquamation | −31.43 | p < 0.1 |

As shown in Table 8, all the signs and symptoms tested improved significantly after 15 days using a hydrating gel with the composition of the invention. All the signs and symptoms tested are direct or indirectly related to the skin microbiome. A reduction in signs or symptoms means a recovery of a balanced microbiome and so a shift from dysbiosis to eubiosis in skin. Thus, the composition of the invention is able to treat skin dysbiosis and transforms dysbiosis to eubiosis.

Example 3.—Xeroderma Dysbiosis

In the skin, desquamation, dryness and other skin dysbiosis signs, due to its high rate of appearance, have been understood as normal. We refer to symptoms like dryness, itching, redness, desquamation and irritability between others.

In the following study, signs and symptoms were studied in a population of subjects with a history of xeroderma dysbiosis. Subjects marked a value in a 0-10 scale where they gave their subjective rate at the beginning and after 15 days using the assigned composition.

Several compositions, formulated as a hydrating gel (Table 9), were applied twice a day, after shower and before going to bed.

Signs/Symptoms to be analyzed:
1. Sensation of dry skin (DS)
2. Itching (I)
3. Redness (R)
4. Desquamation (DQ)
5. Irritability (IR)
6. Cracked skin (CS)
7. Soothing sensation (SS)
8. Increased elasticity (E)
9. Hydration (H)

TABLE 9

| | Comp 3.a (% w/w) | Comp 3.b (% w/w) | Comp 3.c (% w/w) | Comp 3.d (% w/w) | Comp 3.e (% w/w) |
| --- | --- | --- | --- | --- | --- |
| Olive oil | 0.50 | 0.00 | 0.50 | 0.00 | 0.00 |
| TMG | 4.00 | 4.00 | 0.00 | 0.00 | 0.00 |
| Xylitol | 10.00 | 0.00 | 0.00 | 10.00 | 0.00 |
| Olive fruit fluid extract | 0.10 | 0.00 | 0.10 | 0.00 | 0.00 |
| Solvent | 47.70 | 58.30 | 61.70 | 52.30 | 62.30 |
| Humectant | 34.50 | 34.50 | 34.50 | 34.50 | 34.50 |
| Mineral source | 1.00 | 1.00 | 1.00 | 1.00 | 1.00 |
| Surfactant | 1.00 | 1.00 | 1.00 | 1.00 | 1.00 |
| Gelling agent | 0.60 | 0.60 | 0.60 | 0.60 | 0.60 |
| Preservative | 0.50 | 0.50 | 0.50 | 0.50 | 0.50 |
| Vitamin | 0.10 | 0.10 | 0.10 | 0.10 | 0.10 |
| | 100.00 | 100.00 | 100.00 | 100.00 | 100.00 |

The results, as the average intensity of the signs/symptoms indicated above of each group at the beginning of the study (t=0) and after 15 days (t=15) are shown in table 10.

TABLE 10

| | Comp 3.a | | Comp 3.b | | Comp 3.c | | Comp 3.d | | Comp 3.e | |
|---|---|---|---|---|---|---|---|---|---|---|
| | t = 0 | t = 15 | t = 0 | t = 15 | t = 0 | t = 15 | t = 0 | t = 15 | t = 0 | t = 15 |
| DS | 8.0 | 2.0 | 7.2 | 6.6 | 7.2 | 5.0 | 7.4 | 5.0 | 7.8 | 7.6 |
| I | 6.6 | 1.2 | 6.8 | 6.8 | 6.4 | 4.8 | 6.8 | 5.6 | 7.4 | 7.6 |
| R | 6.4 | 2.0 | 6.6 | 6.4 | 6.4 | 6.0 | 6.4 | 5.4 | 6.8 | 7.2 |
| DQ | 7.0 | 1.0 | 6.6 | 6.6 | 6.4 | 5.0 | 7.0 | 5.6 | 7.0 | 6.6 |
| IR | 7.0 | 2.2 | 6.6 | 7.0 | 6.6 | 5.6 | 7.2 | 6.4 | 7.2 | 7.2 |
| CS | 8.4 | 0.4 | 6.8 | 7.2 | 7.4 | 5.2 | 6.8 | 5.0 | 7.6 | 7.0 |
| SS | 1.6 | 9.2 | 3.0 | 3.2 | 2.4 | 4.4 | 2.6 | 4.0 | 1.8 | 2.2 |
| E | 2.2 | 8.6 | 3.0 | 3.4 | 2.8 | 4.4 | 2.6 | 4.6 | 2.2 | 1.6 |
| H | 1.0 | 9.6 | 2.0 | 2.8 | 2.6 | 5.0 | 2.4 | 4.6 | 1.6 | 2.0 |

The reduction in the intensity (int, in the table) of the complaints assessed for each composition and the increase of the beneficial effects for each composition are shown in Table 11.

TABLE 11

| | Change after 15 days | | | | | | | | | |
|---|---|---|---|---|---|---|---|---|---|---|
| | Comp 3.a | | Comp 3.b | | Comp 3.c | | Comp 3.d | | Comp 3.e | |
| | Int | p | Int | p | Int | p | Int | p | Int | p |
| DS | −6 | <0.01 | −0.6 | 0.51 | −2.2 | 0.01 | −2.4 | 0.03 | −0.2 | 0.83 |
| I | −5.4 | <0.01 | 0 | 1 | −1.6 | 0.03 | 1.2 | 0.04 | 0.2 | 0.74 |
| R | −4.4 | <0.01 | −0.2 | 0.81 | −0.4 | 0.61 | −1 | 0.16 | 0.4 | 0.38 |
| DQ | −6 | <0.01 | 0 | 1 | −1.4 | 0.01 | −1.4 | 0.05 | −0.4 | 0.61 |
| IR | −4.8 | <0.01 | 0.4 | 0.53 | −1 | 0.25 | −0.8 | 0.26 | 0 | 1.00 |
| CS | −8 | <0.01 | 0.4 | 0.77 | −2.2 | <0.01 | −1.8 | 0.04 | −0.6 | 0.54 |
| SS | 7.6 | <0.01 | 0.2 | 0.82 | 2 | 0.01 | 1.4 | 0.05 | 0.4 | 0.47 |
| E | 6.4 | <0.01 | 0.4 | 0.69 | 1.6 | 0.01 | 2 | <0.01 | −0.6 | 0.22 |
| H | 8.6 | <0.01 | 0.8 | 0.46 | 2.4 | <0.01 | 2.2 | <0.01 | 0.4 | 0.46 |

Finally, all the complaints average reduction and all the beneficial effects average increase after 15 days of use of gels are represented for all the groups in Table 12.

TABLE 12

| | Comp 3.a | Comp 3.b | Comp 3.c | Comp 3.d | Comp 3.e |
|---|---|---|---|---|---|
| Average of Complaints Reduction | 5.77 | 0.00 | 1.47 | 1.43 | 0.10 |
| Average of Benefits Increase | 7.53 | 0.47 | 2.00 | 1.90 | 0.07 |

Conclusion

Complaints, including signs and symptoms of skin dysbiosis are reduced significantly when using for 15 days the composition of the invention comprising an olive product, betaine and xylitol. Beneficial effects are improved in a much higher quantity after using for 15 days a gel comprising olive product, betaine and xylitol. When comparing the complaints reduction and beneficial improvement obtained with each composition after 15 days of use, a synergistic advantageous effect can be seen with the composition of the invention.

Example 4.—Oral Aphthous Dysbiosis

Oral Aphthous Dysbiosis was assayed in a group of patients with symptoms such as pain and ulcers associated to oral aphthous dysbiosis. Pain and aphthae or ulcer healing were measured and compared between 4 groups using different compositions (Table 13). The products were formulated as a gel and applied before every main meal and before going to bed until aphthae remission. If pain during the day, an extra application was also allowed.

TABLE 13

| | Comp 4.a (% w/w) | Comp 4.b (% w/w) | Comp 4.c (% w/w) | Comp 4.d (% w/w) |
|---|---|---|---|---|
| Olive oil | 0.50 | 0.50 | 0.00 | 0.00 |
| TMG | 4.00 | 4.00 | 0.00 | 0.00 |
| Xylitol | 10.00 | 0.00 | 10.00 | 0.00 |
| Olive fruit fluid extract | 0.10 | 0.10 | 0.00 | 0.00 |
| Solvents | 46.70 | 56.70 | 51.30 | 61.30 |
| Humectant | 34.50 | 34.50 | 34.50 | 34.50 |
| Buffering | 1.50 | 1.50 | 1.50 | 1.50 |

TABLE 13-continued

| | Comp 4.a (% w/w) | Comp 4.b (% w/w) | Comp 4.c (% w/w) | Comp 4.d (% w/w) |
|---|---|---|---|---|
| Mineral source | 1.00 | 1.00 | 1.00 | 1.00 |
| Surfactant | 1.00 | 1.00 | 1.00 | 1.00 |
| Preservative | 0.50 | 0.50 | 0.50 | 0.50 |
| Gelling agent | 0.10 | 0.10 | 0.10 | 0.10 |
| Vitamin | 0.10 | 0.10 | 0.10 | 0.10 |
| | 100.00 | 100.00 | 100.00 | 100.00 |

Sixteen patients were included in the study and separated randomly into the 4 groups. Three parameters were recorded:

1. Time for remission

2. Pain while oral hygiene.

3. Pain while speaking.

The results as the average days required for remission of the aphthae for the 4 groups are shown in Table 14. As seen in the table, patients using the composition comprising Olive oil, Betaine and Xylitol experienced an average ulcer/aphthae healing time of 2.25 days compared to 3.25 days for the group using the composition with Olive oil and Betaine, 5 days for the group using the composition with Xylitol. The control group had to wait more than 7 days on average for ulcer healing. These findings correlate with the measurement of the average intensity of pain during oral hygiene and speaking measured at the beginning of the study (t=0) and after 24 hours (t=24) of using the products, and represented for the 4 groups in Table 15.

TABLE 14

|  | Comp 4.a | Comp 4.b | Comp 4.c | Comp 4.d |
|---|---|---|---|---|
| Remission time | 2.25 | 3.25 | 5.00 | 7.67 |

TABLE 15

|  | Comp 4.a | | Comp 4.b | | Comp 4.c | | Comp 4.d | |
|---|---|---|---|---|---|---|---|---|
|  | t = 0 | t = 24 | t = 0 | t = 24 | t = 0 | t = 24 | t = 0 | t = 24 |
| Pain during oral hygiene | 7.5 | 1.5 | 7.0 | 4.7 | 6.0 | 5.7 | 7.5 | 7.0 |
| Pain during speaking | 7.5 | 1.5 | 7.7 | 5.3 | 7.0 | 4.7 | 9.0 | 8.0 |

The composition of the invention has a synergistic effect in oral dysbiosis such aphthous oral dysbiosis with a statistically significant improvement in ulcer healing and pain management compared to the other compositions.

Traditional management of aphthous dysbiosis is driven by topical analgesics and disinfectants. Hyaluronic acid or/and aloe vera formulations claim a barrier protection for the ulcer but are combined with antiseptics like alcohol in high concentrations. The composition of the invention was able to restore the mucosa barrier function in absence of antiseptics with an immediate relieve of pain.

Pain stopped immediately with possibility of brushing and speaking measured after 24 hours of application. The composition of the invention relieved pain immediately showing a positive summative effect statistically significant with instant pain relief when compared to a composition with olive product and betaine and even more when comparing to a composition with only xylitol as active ingredient (Table 16).

TABLE 16

|  | Comp 4.a | | Comp 4.b | | Comp 4.c | | Comp 4.d | |
|---|---|---|---|---|---|---|---|---|
|  | Difference (diff) | P | Diff | p | Diff | p | Diff | p |
| Pain during hygiene | 6 | <0.01 | 2 | 0.13 | 0.5 | 0.6 | 0.49 | 0.7 |
| Pain while speaking | 6 | <0.01 | 2.3 | 0.06 | 1.5 | 0.4 | 0.46 | 1.7 |

Example 5.—Cold

The mucosa of the lung, as any other mucosa when in eubiosis and benefiting from microbiome homeostasis, enjoys the microbiome moisture action as well as the microbiome defensive protective barrier effect against penetration of detrimental agents experiencing the comfort of hydration, absence of pain, and absence of cough, while on the contrary, the feeling of dehydration, the presence of dry cough and symptoms of cold episodes has been associated with the presence of dysbiosis and a microbiome shift with an increased risk of infections or exacerbation of infections. Age is an initiator of dysbiosis as microbiome loses specificity rendering the elderly patients more vulnerable to infections.

A group of patients tested the preventive effect of the composition of the invention measuring the subjective feeling of hydration of the mucosa and the number of respiratory episodes (colds) using the composition of the invention. Nineteen closure nuns with a mean of 77 years of age accounted the number of cold episodes developed during the time of the study using a topical gel applied through the nose, mouth and throat with the composition of the invention (Table 17) and compared to the number of episodes developed the previous year. They also answered the question "Do you feel your mucosa more hydrated now, Yes or No" (Table 18).

TABLE 17

|  | Comp 5 (% w/w) |
|---|---|
| Olive oil | 1.11 |
| TMG | 4.00 |
| Xylitol | 10.00 |
| Others: Solvent (46.19%), Humectant (34.50%), buffer (1.50%), mineral source (1.00%), surfactant (1.00%), preservative (0.50%), gelling agent (0.10%), vitamin (0.10%) | 85.40 |

TABLE 18

|  | Yes | No |
|---|---|---|
| Answers of patients to the question "Do you feel your mucosa more hydrated now?" | 16 | 3 |

Table 19 shows the number of cold episodes developed by the 19 nuns during the duration of the study compared to the previous year.

TABLE 19

| Cold episodes in the previous year | Cold episodes during the duration of the study | % of reduction | P |
|---|---|---|---|
| 32 | 20 | 37.5 | 0.037 |

As shown in Table 19, the difference in the number of episodes has a statistically significant difference.

The results of this study demonstrate that the use of the composition of the invention can significantly prevent dysbiosis and help to reduce the number of colds.

Example 6.—COPD Dysbiosis

In the following study, change or absence of taste (dysgeusia or ageusia) evolution was studied in a group of 8 patients diagnosed with chronic obstructive pulmonary disease (COPD) a common lung dysbiosis. Patients were divided into 2 groups and each group was treated with 2 different tablets; one including the composition of the invention comprising olive fruit dry extract, betaine and xylitol and one with a commercial suckable tablet with xylitol (Tables 20a and 20b).

TABLE 20a

|  | Comp (%) |
|---|---|
| Olive fruit dry extract | 0.100 |
| TMG | 1.250 |
| Xylitol | 25.000 |

TABLE 20a-continued

| | Comp (%) |
|---|---|
| Others: Aroma (2.400%), Humectant (68.000%), Flow agent (2.925%), Antistatic (0.300%), Vitamin (0.025%). | 73.650 |

TABLE 20b

| |
|---|
| Commercial suckable tablet with xylitol (data obtained from internet manufacturer page) Sweeteners (Xylitol (87%), Aspartame), Aroma, Fully hydrogenated cotton seed oil |

Subjects answered the question "Do you perceive food taste?" before using the tablets and after 5 days of using them.

Results, as the answer to the question at the beginning (t=0) and after 5 days (t=5) sucking 3 tablets per day are in table 21.

TABLE 21

| | Answer to the question: "Do you perceive food taste?" | | | |
|---|---|---|---|---|
| | t = 0 | | t = 5 | |
| | Yes | No | Yes | No |
| Composition of the invention | 4 | | 4 | |
| Commercial composition | 4 | | | 4 |

Patients with dysgeusia or ageusia a common symptom of mucosa dysbiosis and in particular lung dysbiosis, usually suck sweets and/or lozenges to mask the change of taste or improve taste. These tablets are usually flavoured and sweet. In this study the use of commercial tablets, with high concentration of xylitol did not help in recovery of food taste after 5 days. In contrast, the tablets with the composition of the invention had a surprising positive outcome in taste recovery, associated to COPD dysbiosis.

Example 7.—OLP Dysbiosis

Oral Lichen Planus (OLP) is a dysbiosis that can affect either skin, mouth or both. It is treated with corticosteroids. Oral hygiene during the course of the disease is painful and the progression of periodontitis is reluctant and severe in patients with OLP. Eating and hygiene can be impaired in OLP flares.

In this study it was analysed whether the composition of the invention was able to improve the efficacy of corticoids when used in the treatment of an OLP.

Twenty patients with OLP were included in the study.

Two groups of 10 patients each were separated as follows:

Group 1.—Patients treated with corticosteroids and with especial hygiene measures using the composition of the invention as toothpaste (Composition 7.a in Table 22).

Group 2.—Patients treated with corticosteroids and with hygiene measures without the composition of the invention (Composition 7.b in table 22).

TABLE 22

| | Comp 7.a (% w/w) | Comp 7.b (% w/w) |
|---|---|---|
| TMG | 4.0000 | 0.0000 |
| Olive oil | 0.5000 | 0.0000 |
| Olive fruit fluid extract | 0.0500 | 0.0000 |
| Xylitol | 11.0000 | 0.0000 |
| Humectant | 67.6150 | 83.1650 |
| Abrasive | 5.0000 | 5.0000 |
| Mineral source | 8.0500 | 8.0500 |
| Surfactant | 0.8500 | 0.8500 |
| Enzyme | 1.0000 | 1.0000 |
| Aroma | 1.1000 | 1.1000 |
| Sweetener | 0.085 | 0.085 |
| Preservative | 0.5000 | 0.5000 |
| Gelling agent | 0.2000 | 0.2000 |
| Vitamin | 0.0500 | 0.0500 |
| | 100.0000 | 100.0000 |

Treatments lasted 30 days, and a 1 to 10 graduated scale was recovered for pain at the beginning of the study (T0), after 15 days of treatment (T15) and after 30 days of treatment (T30). Results are shown in Table 23.

TABLE 23

| | T0 | T15 | T30 |
|---|---|---|---|
| Corticoids + Composition 7.a | 6.47 | 3.2 | 2.14 |
| Corticoids + Composition 7.b | 6.45 | 4.84 | 4.26 |

As shown in Table 23, the treatment combining corticosteroids with a toothpaste including the composition of the invention improves the efficacy of the corticosteroids after 15 and 30 days of treatment, since less pain was recorded by the patients treated with the composition of the invention.

Example 8.—Halitosis Dysbiosis

Halitosis dysbiosis arises from an oral microbiome shift towards anaerobic bacteria, such as *Porphyromonas gingivalis*, *Treponema denticola* and *Tannerella forsythia* between others. The microbiome shift courses with an environment responsible for inflammation and Volatile Sulfur Compounds (VSC) as a consequence of proteins breakdown. Some of the VSC known are hydrogen sulfide, methyl mercaptan and dimethyl sulfide.

It has been reported that the VSC level present in patients with periodontal dysbiosis disease is found 8-times greater than that of the non-periodontal dysbiosis patients. However, halitosis dysbiosis is also found in dietary restriction, and associated to other oral dysbiosis.

This study investigates the effect of different compositions on halitosis dysbiosis after 4 weeks of use.
Materials and Method Twenty patients diagnosed with halitosis dysbiosis were divided in 4 groups. Each group used one of the four compositions (Table 24) in the form of a mouth spray and used them 3 times a day by spraying twice into the oral cavity.

TABLE 24

| COMPOSITION | Comp 8.a (% w/w) | Comp 8.b (% w/w) | Comp 8.c (% w/w) | Comp 8.d (% w/w) |
|---|---|---|---|---|
| Olive oil | 2.2574 | 2.2574 | 0.0000 | 0.0000 |
| TMG | 2.0000 | 2.0000 | 0.0000 | 0.0000 |
| Xylitol | 20.0000 | 0.0000 | 20.0000 | 0.0000 |

33

TABLE 24-continued

| COMPOSITION | Comp 8.a (% w/w) | Comp 8.b (% w/w) | Comp 8.c (% w/w) | Comp 8.d (% w/w) |
|---|---|---|---|---|
| Humectant | 2.0000 | 2.0000 | 2.0000 | 2.0000 |
| Buffering | 2.1000 | 2.1000 | 2.1000 | 2.1000 |
| Surfactant | 10.0000 | 10.0000 | 10.0000 | 10.0000 |
| Aroma | 2.3200 | 2.3200 | 2.3200 | 2.3200 |
| Sweetener | 1.5100 | 1.5100 | 1.5100 | 1.5100 |
| Preservative | 0.4000 | 0.4000 | 0.4000 | 0.4000 |
| Solvent | 57.4126 | 77.4126 | 61.6700 | 81.6700 |
| | 100.0000 | 100.0000 | 100.0000 | 100.0000 |

Method

VSC measured in the mouth with the use of a device that measures the amount of a sulfur compound.

VSC Results Interpretation

Normal values (no halitosis dysbiosis): From 0 to 100 ppb

Weak halitosis dysbiosis: From 101 to 150 ppb

Strong halitosis dysbiosis: From 151 to 300 ppb

Very strong halitosis dysbiosis: Above 300 ppb

Number of Subjects and Measurement

Twenty patients were included in the study. Initial baseline VSC scores were measured and 4 groups were formed distributing the score patients without allowing statistical differences between the groups. All patients were instructed to use the assigned products for 4 weeks. Final scores were measured at the end of the study and comparisons were made between groups. Two measurements were done, one after the other, and the mean value of the two measurements was calculated.

Results

VSC (ppb) average for each group, at the beginning and the end of the study, are shown in Table 25.

TABLE 25

| | Comp 8.a | Comp 8.b | Comp 8.c | Comp 8.d |
|---|---|---|---|---|
| Initial | 212 | 195.4 | 209 | 188.4 |
| Final | 89.8 | 165.4 | 170 | 198.4 |
| p | <0.001* | 0.095 | <0.218 | <0.71 |

*statistically significant.

A decrease in VSC after 4 weeks using the tested compositions was observed for composition 8.a (122.2 ppb), composition 8.b (30 ppb) and composition 8.c (39 ppb), while a light increase was observed for the composition 8.d (10 ppb).

Conclusions

The composition of the invention (comp 8.a), comprising xylitol, olive oil and betaine, shows a beneficial effect on halitosis dysbiosis. Surprisingly, a synergistic improvement was obtained with the composition of the invention in comparison with compositions 8.b and 8.c, which lack xylitol and olive oil, respectively.

Example 9.—Sleep Apnea and Tooth Wear Dysbiosis

As explained in the description of the invention, the microbiome protects teeth from challenges in conditions of symbiosis. In stress, tooth wear and sleep apnea oral dysbiosis as well as oral dysbiosis associated to eating disorders or gastric reflux, the disruption or alteration of the microbiome leads to tooth hypersensitivity and demineralization. When the microbiome is altered or disrupted, hypersensitivity, demineralization, caries and/or tooth wear happen (e.g. due to bruxism, erosion, abfraction, attrition) and teeth start to dissolve in acidic or extremely acidic media, being hypersensitivity the first symptom of these dysbiosis.

Materials and Method

Eight patients diagnosed with sleep apnea dysbiosis and showing tooth wear and hypersensitivity were recruited and separated into two groups.

The first group was treated with a traditional commercial hypersensitivity gel and mouthwash containing a source of fluoride (sodium fluoride) and potassium nitrate. The content of said ingredients is known, but the rest of the quantitative composition is unknown so it is not depicted in Table 26.

The second group was treated with the composition of the invention applied in a mouthwash and a gel. Compositions for both groups are shown in Table 26 were composition 9.a is a mouthwash with the composition of the invention, composition 9.b is a gel with the composition of the invention, composition 9.c is the commercial mouthwash and the composition 9.d is the commercial gel.

Patients applied the mouthwash 3 times a day for two minutes after brushing, and applied the gel topically onto the oral cavity after rinsing in the morning and before bed time. Treatment lasted 15 days for both groups.

TABLE 26

| | Comp 9.a (% w/w) | Comp 9.b (% w/w) | Comp 9.c (% w/w) | Comp 9.d (% w/w) |
|---|---|---|---|---|
| Olive oil | 2.000 | 1.110 | | |
| TMG | 2.000 | 4.000 | | |
| Xylitol | 1.000 | 10.000 | | |
| Olive fruit fluid extract | | 0.100 | | |
| Potassium nitrate | | | 10.000 | 5.000 |
| Sodium fluoride | | | 0.220 | 0.320 |
| Humectant | 7.000 | 34.500 | | |
| Buffering | 0.855 | 1.500 | | |
| Surfactant | 12.000 | 1.000 | | |
| Aroma | 0.405 | | | |
| Sweetener | 0.025 | | | |
| Preservative | 0.700 | 0.500 | | |
| Solvent | 73.282 | 46.090 | | |
| Vitamin | 0.300 | 0.100 | | |
| Mineral source | 0.183 | 1.000 | | |
| Healing agent | 0.200 | | | |
| Colourant | 0.050 | | | |
| Gel forming agent | | 0.100 | | |

Method

Self-reported answers to the following questions were recorded:

Can you drink cold water?

Can you eat a piece of fruit from the refrigerator?

Do you feel sensitivity while brushing your teeth?

Do you feel your mouth hydrated?

Do you brux your teeth during night?

Results

Answers to the questions for both groups before and after 15 days treatment are shown in the Table 27, wherein the number of subjects saying Yes or No are shown.

TABLE 27

| | Comp 9.a and 9.b | | | | Comp 9.c and 9.d | | | |
|---|---|---|---|---|---|---|---|---|
| | Before | | After | | Before | | After | |
| | Yes | No | Yes | No | Yes | No | Yes | No |
| Can you drink cold water? | 0 | 4 | 4 | 0 | 0 | 4 | 1 | 3 |
| Can you eat a piece of fruit from the refrigerator? | 0 | 4 | 4 | 0 | 0 | 4 | 2 | 2 |
| Do you feel sensitivity while brushing your teeth? | 4 | 0 | 0 | 4 | 4 | 0 | 3 | 1 |
| Do you feel your mouth hydrated? | 0 | 4 | 4 | 0 | 0 | 4 | 0 | 4 |
| Do you brux your teeth during night? | 4 | 0 | 0 | 4 | 4 | 0 | 3 | 1 |

Conclusions

While the group using the composition of the invention had a 100% improvement of the symptoms outcome, the groups using the commercial products did not have any improvement (hydration) or improved only from 25 to 50% (rest of the symptoms).

The invention claimed is:

1. A method of treating dysbiosis in a human in need thereof comprising administering topically a therapeutic effective amount of a composition comprising an olive oil and/or olive fruit extract, betaine, and xylitol to said human, wherein the composition comprises 0.05%-5.1% by weight of the olive oil and/or olive fruit extract, 0.1%-10% by weight of betaine, and 1%-25% by weight of xylitol.

2. The method of claim 1, wherein the dysbiosis is mucosa dysbiosis or skin dysbiosis.

3. The method of claim 2, wherein the mucosa dysbiosis is oral dysbiosis.

4. The method of claim 2, wherein the dysbiosis is skin dysbiosis.

5. The method of claim 2, wherein the mucosa dysbiosis is vagina dysbiosis.

6. The method of claim 2, wherein the mucosa dysbiosis is lung dysbiosis.

7. The method of claim 3, wherein the oral dysbiosis is selected from the group consisting of halitosis dysbiosis, caries dysbiosis, periodontal dysbiosis, aphthous dysbiosis, periimplantitis dysbiosis, Lichen Planus dysbiosis, Pemphigus dysbiosis, sleep apnea dysbiosis, stress dysbiosis, tooth wear dysbiosis, diabetes oral dysbiosis, cancer oral dysbiosis, and combinations thereof.

8. The method of claim 4, wherein the skin dysbiosis is selected from the group consisting of atopic dermatitis dysbiosis, acne vulgaris dysbiosis, psoriasis dysbiosis, xeroderma dysbiosis, skin allergies dysbiosis, radiodermatitis dysbiosis, solar dermatitis dysbiosis, contact dermatitis dysbiosis, seborrheic dermatitis dysbiosis, scalp dysbiosis, body malodor dysbiosis, premature skin aging dysbiosis, Lichen Planus dysbiosis, Pemphigus dysbiosis, and combinations thereof.

9. The method of claim 6, wherein the lung dysbiosis is selected from the group consisting of chronic pulmonary dysbiosis, chronic obstructive pulmonary dysbiosis, cystic fibrosis dysbiosis, asthma dysbiosis, tracheitis dysbiosis, bronchitis dysbiosis, infectious respiratory dysbiosis.

10. The method of claim 1, wherein the olive fruit extract is olive fruit dry extract and/or olive fruit liquid extract; and/or wherein the olive fruit extract comprises at least 20% w/w of hydroxytyrosol; and/or wherein the olive oil is extra virgin olive oil, virgin olive oil, or a combination thereof; and/or wherein betaine is selected from the group consisting of trimethylglycine, cocamidopropyl betaine, dimethylamine betaine, alkyl ($C_{12}$-$C_{18}$) amido betaines, alkyl ($C_8$-$C_{18}$) betaines, amidobetaines, alkyl amido betaines, sulpho hydroxy betaines and combinations thereof.

11. The method of claim 1, wherein the composition comprises 0.05%-2.6% by weight of the olive oil and/or olive fruit extract.

12. The method of claim 1, wherein the composition comprises 1.0%-6% by weight of betaine.

13. The method of claim 1, wherein the composition comprises 1%-20% by weight of xylitol.

14. The method of claim 1, wherein the composition comprises 0.05%-5.1% by weight of the olive oil and/or olive fruit extract, 0.1%-10% by weight of betaine, and 1%-20% by weight of xylitol.

15. The method of claim 1, wherein the composition additionally comprises one or more antioxidants, vitamins, prebiotics, and/or probiotics.

16. The method of claim 1, wherein the composition comprises the olive oil and/or olive fruit extract, betaine and xylitol as the only active ingredients.

* * * * *